(12) United States Patent
Ogawa et al.

(10) Patent No.: US 7,808,237 B2
(45) Date of Patent: Oct. 5, 2010

(54) METHOD AND INSTRUMENT OF LOCALLY MEASURING PROTIC SOLVENT CONTENT IN SAMPLES

(75) Inventors: Kuniyasu Ogawa, Kanagawa (JP); Tomoyuki Haishi, Ibaraki (JP); Kohei Ito, Fukuoka (JP)

(73) Assignee: Keio University, Tokyo (JP)

( * ) Notice: Subject to any disclaimer, the term of this patent is extended or adjusted under 35 U.S.C. 154(b) by 464 days.

(21) Appl. No.: 11/575,173

(22) PCT Filed: Sep. 12, 2005

(86) PCT No.: PCT/JP2005/016771

§ 371 (c)(1),
(2), (4) Date: Mar. 13, 2007

(87) PCT Pub. No.: WO2006/030743

PCT Pub. Date: Mar. 23, 2006

(65) Prior Publication Data

US 2009/0140736 A1    Jun. 4, 2009

(30) Foreign Application Priority Data

Sep. 13, 2004   (JP)   ............................. 2004-265535
Apr. 15, 2005   (JP)   ............................. 2005-118138

(51) Int. Cl.
 *G01V 3/00*   (2006.01)
(52) U.S. Cl. ...................................... 324/300; 324/303
(58) Field of Classification Search ................. 324/300, 324/303, 318
See application file for complete search history.

(56) References Cited

U.S. PATENT DOCUMENTS

| | | | |
|---|---|---|---|
| 6,522,137 B1 * | 2/2003 | Sun et al. | 324/303 |
| 7,208,953 B2 * | 4/2007 | Kurihara et al. | 324/318 |
| 7,345,479 B2 * | 3/2008 | Park et al. | 324/300 |

FOREIGN PATENT DOCUMENTS

| | | |
|---|---|---|
| JP | 51-127785 | 11/1976 |
| JP | 60-190846 | 9/1985 |
| JP | 02-065844 | 3/1990 |
| JP | 06-288943 | 10/1994 |
| JP | 07-198635 | 8/1995 |
| JP | 07-255700 | 10/1995 |
| JP | 2001-106728 | 4/2001 |
| JP | 2004-170297 | 6/2004 |

OTHER PUBLICATIONS

Becker et al, Pulse Oyobi Fourier Henkan NMR, Pulse and Fourier Transform NMR: Introduction to Theory and Methods, 1976, pp. 30-38.

(Continued)

Primary Examiner—Louis M Arana
(74) Attorney, Agent, or Firm—Turocy & Watson, LLP

(57) ABSTRACT

Excitation-use high frequency RF generated by an RF oscillator is modulated by a modulator based on control by a pulse control unit, to give a pulse form. The generated RF pulse is then amplified by an RF amplifier, and set to a small-sized RF coil. The small-sized RF coil applies the RF pulse to a specific position of a sample placed on a sample stage, and detects echo signals of the RF pulse. The echo signal is amplified by a preamplifier, and is then sent to a phase detector. The phase detector detects the echo signal, and sent it via an A/D converter to an operation unit. The operation unit calculates $T_2$ relaxation time constant based on intensity of the echo signal, and the water content at the predetermined position of the sample is calculated based on the calculated $T_2$ relaxation time constant.

30 Claims, 21 Drawing Sheets

OTHER PUBLICATIONS

Armenean et al, Solenoidal and Planar Microcoils for NMR Spectroscopy, 2003, vol. 4, pp. 3045-3048.

Ito et al, Investigation of Water Molecule Concentration Distribution and Transport Coefficient in Solid Polymer Electrolyte Membrane by Magnetic Resonance Imaging, 2002, vol. 68, No. 666, pp. 253-259.

Ogawa et al, Development of a Local NMR Sensor for Wetness Monitoring of Polymer Electrolyte Membrane Using a Planar Surface Coil, 2005, pp. 99-100.

International Search Report for PCT/JP2005/016771 dated Nov. 22, 2005.

* cited by examiner

Fig.3
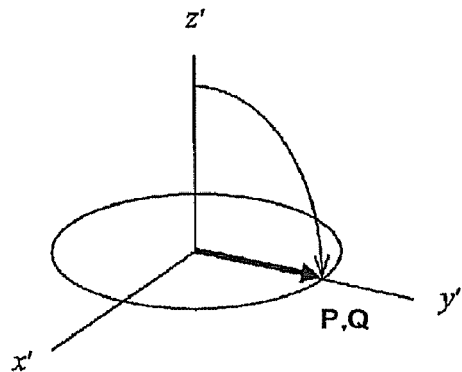
(a) t=0
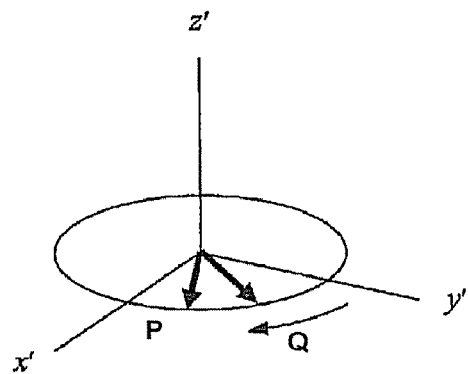
(b) t<τ
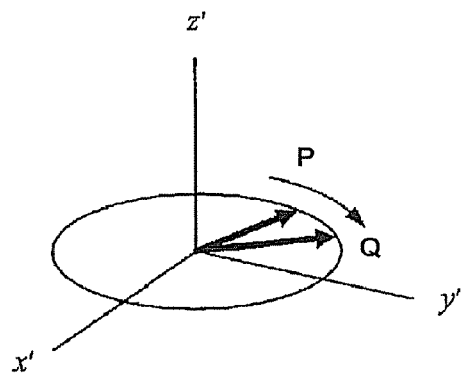
(c) τ<t
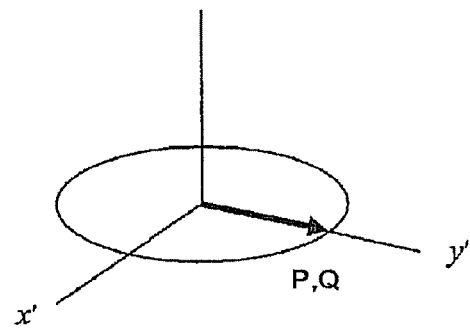
(d) t=2τ

| Sample | $T_2$(CPMG) | Outside diameter of planar surface coil | | Standard solenoidal coil |
|---|---|---|---|---|
| | | 0.8 mm | 2.0 mm | 25 mm |
| 1.2 mmol/l CuSO₄ aq. | Average | 747 ms | 459 ms | 485 ms |
| | (Ratio of average) | (1.54) | (0.946) | (1) |
| | Standard deviation | 118 ms | 52 ms | 6.1 ms |
| | Coefficient of variation | 0.16 | 0.11 | 0.013 |
| 0.1 mmol/l CuSO₄ aq. | Average | 1700 ms | 1370 ms | 1290 ms |
| | (Ratio of average) | (1.32) | (1.062) | (1) |
| | Standard deviation | 232 ms | 178 ms | 7.5 ms |
| | Coefficient of variation | 0.14 | 0.13 | 0.006 |

| COIL | $T_2$ (CPMG) [ms] |
|---|---|
| SMALL-SIZED SURFACE COIL (1st CHANNEL) | 1280 |
| SMALL-SIZED SURFACE COIL (2nd CHANNEL) | 1350 |
| LARGE-SIZED SOLENOID COIL | 1290 (7.5 ms VARIATION IN MEASUREMENT) |
| SMALL-SIZED SURFACE COIL (SINGLE) | 1370 (170 ms VARIATION IN MEASUREMENT) |

METHOD AND INSTRUMENT OF LOCALLY MEASURING PROTIC SOLVENT CONTENT IN SAMPLES

TECHNICAL FIELD

The present invention relates to a method and an instrument of locally measuring protic solvent content in samples.

BACKGROUND ART

In the past, trials have been made on measuring relaxation time constant by $^1$H-NMR, and applying the results to material development. Patent Document 1 relates to one example of this sort of techniques.

Patent Document 1 discloses use of parameters including $^1$H-NMR transverse relaxation time constant, in the process of designing waterabsorbent polymer used for paper diaper and so forth. In this document, $^1$H-NMR transverse relaxation time constant is understood as a parameter relevant to mobility of molecular chains of the resin, and it is concluded that shorter transverse relaxation time is indicative of higher degrees of entanglement and crosslinking of the polymer chains.

In this literature, the transverse relaxation time constant is determined by the CPMG (Carr-Purcell-Meiboom-Gill) method.

[Patent Document 1] Japanese Laid-Open Patent Publication No. 2001-106728

DISCLOSURE OF THE INVENTION

However, only a few examples of development has been known as for technologies applying this sort of results of the NMR measurement to measurement of protic solvent content in substances, in particular for measurement of protic solvent content (water content, for example) at specific positions in substances.

It may otherwise be possible to calculate water content in substances, if spin relaxation time constant is determined with respect to water molecules (protic solvent) which reside in substances. It is also possible on the principle basis to locally measure the water content, if a technique of applying a gradient magnetic field is used. However, the technique of applying the gradient magnetic field, is not practical, because it needs a measurement time of as long as 100 seconds or more. In particular, for the case where a system of using results of the measurement for feed-back control, such as locally measuring water content at a specific position in a substance and then supplying water to the substance based on results of the measurement, is adopted, the elongation of the measurement time described in the above raises a serious problem.

The present invention was conceived after considering the above-described situation, and is to provide a technique of measuring local protic solvent content at a specific position in substances, using results of NMR measurement, within a relatively short period of time.

According to the present invention, there is provided a method of locally measuring protic solvent content of a sample at a specific position thereof using a nuclear magnetic resonance method, which include:

a first step sequentially applying plural number of times an excitation-use oscillating magnetic field to a specific position of the sample disposed in a static magnetic field, using a small-sized RF coil smaller than the sample, and thereby obtaining a plurality of echo signals corresponded to the excitation-use oscillating magnetic field;

a second step calculating a $T_2$ relaxation time constant based on intensity of the plurality of echo signals; and a third step of acquiring data expressing a correlation between the protic solvent content in the sample and the $T_2$ relaxation time constant, and determining the protic solvent content at the specific position in the sample, based on the data and the $T_2$ relaxation time constant calculated in the second step.

According to the present invention, there is also provided an instrument of locally measuring protic solvent content of a sample at a specific position thereof using a nuclear magnetic resonance method, comprising:

a static magnetic field application unit applying a static magnetic field to the sample;

a small-sized RF coil smaller than the sample, applying an excitation-use oscillating magnetic field to the sample, and acquiring an echo signal corresponded to the excitation-use oscillating magnetic field;

and an operation unit calculating a $T_2$ relaxation time constant based on intensity of the echo signal, and calculating the protic solvent content of the sample at the specific position thereof, based on the calculated $T_2$ relaxation time constant.

In the present invention, the small-sized RF coil is used (i) to locally apply the excitation-use oscillating magnetic field, and (ii) to acquire an echo signal emitted from the position where the excitation-use oscillating magnetic field was applied, then the $T_2$ relaxation time constant (transverse relaxation time constant) is determined based on the echo signal, and based on the time constant, the protic solvent content, typically water content, is measured. Because the pulse echo method is adopted herein, while limiting the portion to be measured by the small-sized RF coil, the local protic solvent content can be measured within a short period of time.

In this patent specification, it is not always necessary for the "static magnetic field" to have complete stability, instead allowing a slight degree of fluctuation, so far as the magnetic field is stable enough, on the time basis, to allow stable acquisition of the echo signal and the $T_2$ relaxation time constant.

Again in this patent specification, it is good enough for the "echo signal" to be a signal corresponded to the excitation-use oscillating magnetic field, and capable of functioning as an NMR signal from which the $T_2$ relaxation time constant can be calculated.

Moreover, in this patent specification, protic solvent means solvents capable of producing proton(s) by dissociating themselves. The protic solvent can be exemplified by water;

alcohols such as methanol and ethanol;

carboxylic acids such as acetic acid;

phenol; and liquid ammonia.

Of these, water or alcohol selected as the protic solvent can ensure more stable measurement of protic solvent content in the present invention.

The excitation-use oscillating magnetic field may be configured as a pulse sequence composed of:

(a) a 90° pulse; and (b) "n" 180° pulses which start after the elapse of time τ following the pulse (a), applied at time 2T intervals. By this configuration, the $T_2$ relaxation time constant can be determined in an accurate manner.

The 90° pulse herein may reside in a first phase, and "n" 180° pulses may reside in a second phase shifted 90° from the first phase. In the actual measurement system, non-uniformities in the static magnetic field and the excitation-use oscillating magnetic field may occur, and may be causative of measurement errors in the $T_2$ relaxation time constant. Whereas, the pulse sequence configured as described in the above adopts, as the 180° pulse, a pulse which resides in the second phase 90° shifted from the first phase, so that application of the 180° pulse inverts the magnetization of nuclei in the rotational coordinate system, and thereby causal factors for the measurement errors ascribable to the aforementioned non-uniformities in the magnetic fields can be cleared. The second phase 180° pulse is periodically applied, and can thereby clear the causal factors for the measurement errors every time it is applied, so that accurate $T_2$ relaxation time constant can be obtained in a reliable manner.

In addition to the above-described pulse sequence, it is also allowable to execute another sequence added with a step of applying a 180° pulse, time τ earlier than the 90° pulse. By comparing intensity of an NMR signal acquired according to the 90° pulse (a), with intensity of an NMR signal acquired at appropriately selected time τ according to the 180° pulse (b), it is made possible to judge whether intensity of the excitation-use oscillating magnetic field irradiated by the small-sized RF coil exactly corresponds to 90° and 180° or not. Keeping a 1:2 relation of the intensities of two pulses, and excitation of the magnetization vector up to 90° and 180°, respectively, are essential factors for improving probability and reproducibility of the measured values. By this configuration, any abnormalities can be detected in the stage prior to the measurement, even when the relation between two pulses was inadequate due to abnormalities in the instrument or unskilled adjustment, and thereby the measurement values can be made more probable.

The present invention may be configured as further having an RF signal generation unit generating an RF signal which allows the small-sized RF coil to generate the excitation-use oscillating magnetic field;

an echo signal detection unit detecting the echo signal acquired by the small-sized RF coil, and sending the echo signal to the operation unit; and a switching circuit provided at a branching portion to which the small-sized RF coil, the RF signal generation unit and the echo signal detection unit are connected, and toggled between a state of connection of the small-sized RF coil and the RF signal generation unit, and a state of connection of the small-sized RF coil and the echo signal detection unit.

This configuration contributes to reduce loss of the excitation-use high frequency pulse signal applied from the small-sized RF coil to the sample, and consequently to exactly control pulse angles of the 90° pulse and the 1800 pulse.

The present invention may be configured also as being provided with a plurality of small-sized RF coils, applying the excitation-use oscillating magnetic field to a plurality of positions of the sample, so as to acquire echo signals corresponded to the excitation-use oscillating magnetic field, calculating the $T_2$ relaxation time constant for each of the plurality of positions of the sample, and determining water content for each of the plurality of positions of the sample, based on the $T_2$ relaxation time constant.

The present invention may be configured still also as presenting, posterior to determination of water content for the plurality of positions, a water content distribution of the sample based on the water contents determined for the plurality of positions of the sample.

This configuration allows multi-point simultaneous measurement based on a simple configuration. Arrangement of the plurality of small-sized RF coils is arbitrary, allowing an arrayed arrangement depending on geometry or the like of the object to be measured.

The instrument of the present invention may be configured also as having a storage unit keeping, by types of the samples, information expressing a correlation between the water content of the sample and the $T_2$ relaxation time constant, which is typically an analytical curve, wherein the operation unit acquires the information corresponded to the sample to be measured from the storage unit, and calculates the water content based on the information.

In the present invention, the sample may include a matrix composed of solid or gel, and the operation unit may be configured as calculating water content in the matrix.

In the present invention, the sample may typically be a water-containing membrane, and may typically be a solid electrolyte membrane (polymer membrane) used for fuel cells and so forth. Measurement of water content in these membranes allows clear understanding of characteristics and properties of the membrane, and state of the membrane in an environment in which the membrane is disposed, and quantitative presentation of properties of the membrane targeted at in the material development.

Also, in the present invention, the sample may be a water-containing liquid, and the operation unit may be configured as calculating water content in the liquid.

According to the present invention adopting a configuration based on use of the small-sized coil, and local application of the multi-echo method to a specified position of the sample, local water content at the specified position of the sample can be measured within a short period of time.

Further, in the present invention, the small-sized RF coil is preferably a planar coil which comprises a coil portion having a right-handed lead wire, and a coil portion having a left-handed lead wire, linked to each other.

By using a flat-type, small-sized RF coil, which is so-called an 8-figure coil having a pair of coil portions linked to each other, the water content can be measured in a more accurate manner.

Furthermore, the measurement instrument of the present invention may be configured as having a support supporting the small-sized RF coil and the static magnetic field application unit, wherein the support has a stick form, and has the small-sized RF coil attached to the end portion thereof.

This configuration allows the user to hold the support, and to perform measurement simply by bringing the end portion thereof close to the sample, making it possible to improve the operability of the measurement instrument.

The method of measurement and the measurement instrument of the present invention can locally calculate the protic solvent content of the sample, which is for example water content, within a short period of time. The present invention is therefore applicable to measurement of water content in membranes, measurement of water content distribution and so forth. For example, the present invention is preferably applicable to techniques of controlling amount of supply of water into a fuel based on the calculated water content, such as a system measuring water content of a solid electrolyte membrane (polymer membrane) of a hydrogen-supplied fuel cell in a real-time manner.

According to the present invention, there can be provided, for example, a fuel cell system which includes:

a fuel cell composed of a polymer membrane, and anode and cathode opposed while placing the polymer membrane in between;

an oxidizing gas supply unit supplying an oxidizing gas to the fuel cell;

a fuel gas supply unit supplying a fuel gas to the fuel cell;

a water vapor mixing unit mixing water vapor with the fuel gas discharged from the fuel gas supply unit towards the fuel cell, and supplying the fuel gas and the water vapor to the fuel cell;

any one of the above-described measurement instruments measuring water content of the polymer membrane; and a control unit acquiring results of measurement of water content sent from the measurement instrument, and controlling the water vapor mixing unit based on the results of measurement, so as to adjust the amount of supply of water vapor to be supplied from the water vapor mixing unit.

BRIEF DESCRIPTION OF THE DRAWINGS

The above and other objects, advantages and features of the present invention will be more apparent from the following description of preferred embodiments taken in conjunction with the accompanying drawings, listed below.

FIGS. 3(a) to (d) are drawings explaining a compensation function of the CPMG method;

BEST MODES FOR CARRYING OUT THE INVENTION

Figure 1:
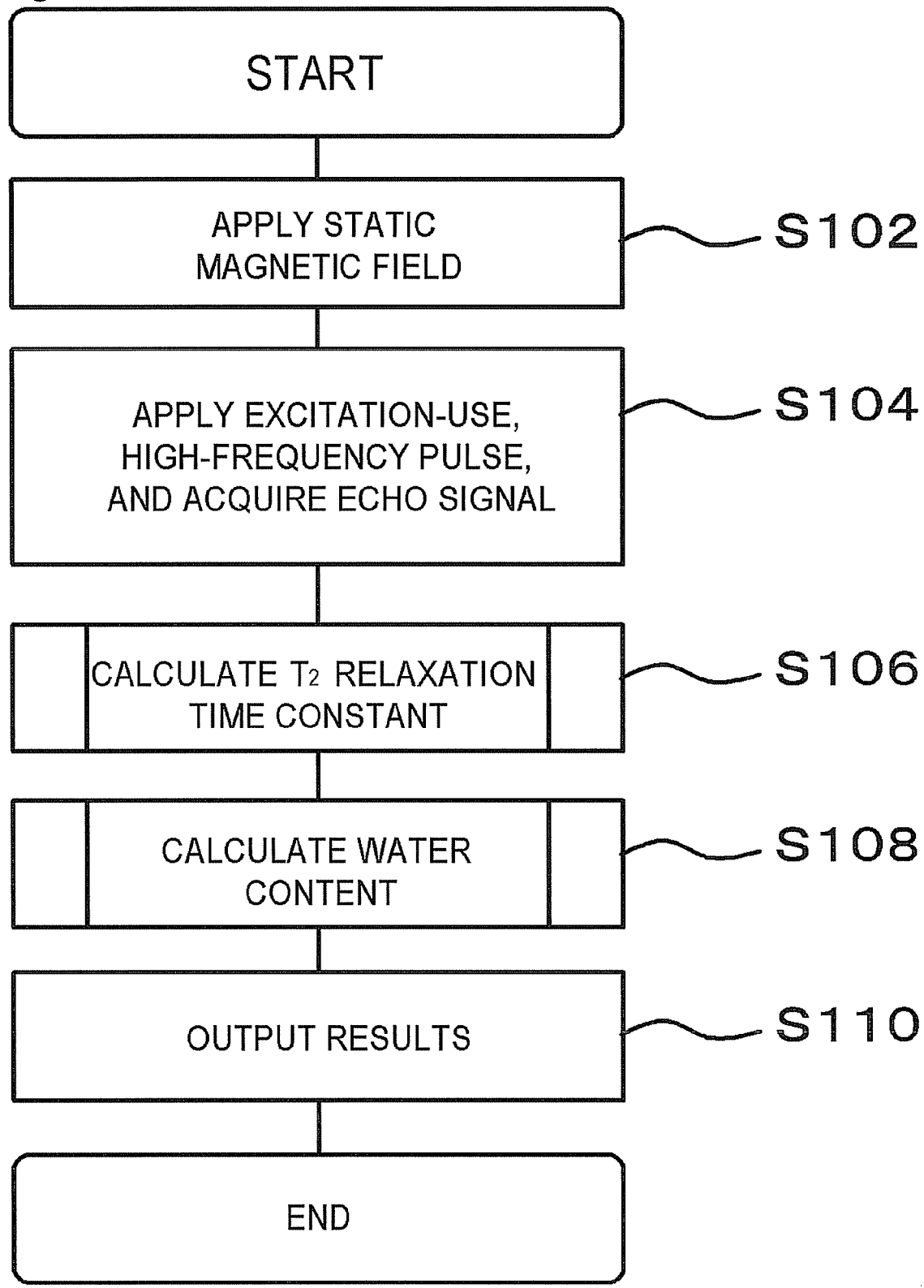
FIG. 1 is a flow chart showing an outline of a method of locally measuring water according to one embodiment.

Embodiments of the present invention will be explained referring to the drawings. In the embodiments described below, the cases of using a high frequency pulse sequence as the excitation-use oscillating magnetic field will be explained. In all of these drawings, any similar constituents will be given with similar reference numerals, so as to occasionally avoid repetitive explanation.

(Principle of Measurement)

The explanation will be begun with procedures of measuring protic solvent content in the individual embodiments described later, in conjunction with the principle of measurement.

The following explanation will be made referring to water as the protic solvent to be measured.

FIG. 1 is a flow chart showing an outline of the method of measuring local water according to this embodiment. First, a sample is placed in a space having a magnet arranged therein, and is applied with a static magnetic field (S102). While keeping this state, the sample is applied with an excitation-use high frequency pulse, and an echo signal corresponded thereto is acquired (S104). Next, a $T_2$ relaxation time constant is calculated based on the echo signal (S106) Local water content of the sample is then measured based on the $T_2$ relaxation time constant (S108). More specifically, data expressing a correlation between water content of the sample and the $T_2$ relaxation time constant is acquired, and the local water content at a predetermined position of the sample is determined, based on the data and the $T_2$ relaxation time constant. Result is then output (S110). Paragraphs below will detail the individual steps.

(i) Step 104 (Application of Excitation-Use High Frequency Pulse and Acquisition of Echo Signal)

Step 104 will be detailed below. In step 104, the sample is applied with the excitation-use high frequency pulse, wherein the excitation-use high frequency pulse is preferably configured as a pulsed sequence composed of a plurality of pulses, so as to acquire a correspondent echo signal group. By adoption of this configuration, the $T_2$ relaxation time constant can be determined in an exact manner. The pulse sequence is preferably composed of:

(a) a 90° pulse, and (b) "n" 180° pulses which start after the elapse of time τ following the pulse (a), applied at time 2T intervals.

In order to clearly understand the correlation between the $T_2$ relaxation time constant and water content of the sample, it is important to appropriately adjust a method of applying the oscillating magnetic field. Adoption of the above-described pattern helps clear understanding of the correlation between the $T_2$ relaxation time constant and water content of the sample. According to the method using the above-described pulse sequence, after the elapse of time τ following the 90° excitation pulse, the 180° excitation pulse having doubled intensity is applied, so as to invert phase disturbance of magnetization vector M, which has been disturbing in progress on the x-y plane (rotational coordinate system), and to make the phase converge after the elapse of time 2τ, and thereby an echo signal fitted to the $T_2$ attenuation curve can be obtained.

By configuring the pulse sequence as having the 90° pulse as residing in the first phase, and "n" 180° pulses as residing in the second phase shifted 90° from the first phase, stable acquisition of clear correlations between the $T_2$ relaxation time constant and water content of the sample is realized. The CPMG method is one example of a method giving such pulse sequence. While Hahn's echo method is known as a way of giving the $T_2$ relaxation time constant used for measurement of the $T_2$ relaxation time constant, the CPMG method is more suitable for measurement of water content. Paragraphs below will explain the CPMG method and comparison between the CPMG method and Hahn's echo method.

[CPMG Method]

Hydrogen nucleus placed in the static magnetic field has a net magnetization vector in the direction along the static magnetic field (referred to as Z-direction, for convenience sake), wherein the magnetization vector inclines in the positive direction of the Y-axis when externally irradiated by an RF wave at a particular frequency (referred to as resonance frequency) in the direction of the X-axis perpendicular to the Z-axis, allowing us to observe a nuclear resonance signal (referred to as an NMR signal). The excitation pulse irradiated in the direction of the X-axis herein so as to acquire the NMR signal of a maximum intensity is referred to as 90° pulse.

In general Hahn's echo method, the magnetization vector is inclined by the 90° pulse into the positive direction of the Y-axis, and after the elapse of time τ, then inverted into the negative direction of the Y-axis by externally irradiating the 180° excitation pulse (having doubled energy of the 90° pulse) in the direction of X-axis after the elapse of additional time τ. As a consequence, the magnetization vector converges in the negative direction of the Y-axis after the elapse of time 2τ, allowing us to observe an signal echo having a large amplitude. The $T_2$ (transverse) relaxation time constant in Hahn's echo method can be calculated by fitting peak intensities of the echo signals to an exponential function, by sequentially altering time intervals τ between the 90° and 180° pulses.

On the other hand, the CPMG method gives the a pulse sequence as shown in FIG. 2(a), and obtains echo signals as shown in FIG. 2(b). First, the magnetization vector is inclined in the positive direction of the Y-axis with the aid of the 90° pulse, and after the elapse of time τ, the magnetization vector is inverted "assuming the Y-axis as the axis of symmetry", by externally irradiating the 180° excitation "in the direction of Y-axis" (differing from Hahn in that the X-axis and the Y-axis are exchanged, meaning that an excitation waveform causing 90° phase shifting is obtained). As a consequence, the magnetization vector converges onto the "positive direction" of the Y-axis after the elapse of time 2τ, allowing us to observe an echo signal having a large amplitude. Further after the elapse of time 3τ, the magnetization vector is externally irradiated with the 180° excitation pulse "in the direction of Y-axis", and is again converged onto the "positive direction" of the Y-axis, allowing us to observe an echo signal having a large amplitude after the elapse of time 4T. Irradiation of the 180° pulses is continued similarly at 2τ intervals. In this process, the $T_2$ (transverse) relaxation time constant based on the CPMG method can be calculated, by extracting intensity of every even-numbered echo signal, such as 2τ, 4τ, 6τ, . . . , and fitting them into an exponential function.

The CPMG method can raise a compensation function described later, since the magnetization vector is inverted assuming the "Y-axis as an axis of symmetry" as described in the above.

[Difference Between Hahn's Echo Method and CPMG Method]

Hahn's echo method and the CPMG method differ in the aspects below.

(i) In the CPMG method, the 180° excitation pulse is in the direction of the Y-axis, and the converged echo is obtained only in the positive direction of the Y-axis. In Hahn's echo, the convergence of the echo signal moves from the positive to negative direction of the Y-axis.

(ii) In the CPMG method, (a) non-uniformity in the static magnetic field, and (b) non-uniformity in the excitation pulse intensity irradiated by the RF coil can be compensated even if they should occur, and thereby an accurate $T_2$ relaxation time constant can be measured.

(iii) The CPMG method uses, as a compensation function, the 180° excitation pulses always allowing the phase to converge into the same positive direction of the Y-axis, so as to avoid irreversible phase dispersion process ascribable to (a) and (b) described in the above.

Additional explanations of (a) and (b) described in the above will be given below.

(a) The non-uniformity in the static magnetic field is caused by the factors below.

The magnet per se is not in a completely uniform magnetic field, for some reasons of the manufacturing processes;

Non-uniformity in the magnetic field occurs due to difference in magnetic susceptibility respectively owned by the sample as an object to be measured, the container housing the sample and the ambient air.

Non-uniformity in the magnetic field occurs due to difference in magnetic susceptibility respectively owned by materials composing the instrument, such as RF coil and container and so forth.

Non-uniformity in the magnetic field occurs due to distortion of the magnetic field as being affected by ambient environment in which the instrument is installed, such as geomagnetism, buildings, floor material and so forth.

Non-uniformity in the magnetic field occurs due to time-dependent fluctuation or spatial gradient of temperature of the magnet, such that the magnet is affected by the ambient environment in which it is placed, and causes fluctuation or distribution of the temperature.

(b) The non-uniformity in intensity of the excitation pulse irradiated by the static magnetic field is caused by the factors below:

A coil having a finite length causes different intensities of excitation pulse to be irradiated, depending on the position thereof. For example, the excitation pulse becomes strong at the center, but is weakened towards the end. Non-uniformity in intensity of the excitation pulse thus occurs.

Non-uniformity in the excitation pulse occurs because of difficulty in symmetrical winding of a lead at regular intervals in the process of manufacturing of the coil, and because the winding becomes inevitably anti-symmetrical in the wiring portion thereof where the coil is connected to a condenser so as to compose a resonant circuit.

It is difficult to adjust the pulse intensity to be irradiated completely to those of the "90°" and "180°" excitation pulses, while being affected also by two above-described factors.

[Compensation Function of the CPMG Method]

The compensation function of the CPMG method, described in the above, will be explained referring to FIG. 3. It is to be noted that the coordinate shown in the drawing is a rotational coordinate system. Assuming now, in the sample, P and Q as nuclear magnetization in an area enough as small as making non-uniformity in the stateic magnetic field negligible. The magnetic field at P is assumed as stronger than the magnetic field at Q. When the 90° pulse is applied in the direction of the x'-axis as shown in FIG. 3($a$), the nuclear magnetizations P, Q starts precession from the same place (y'-axis) in the rotational coordinate system, and the phase of P advances ahead of the phase of Q with elapse of time (FIG. 3($b$)). When the 180° pulse is applied in the direction of the y'-axis, after the elapse of time $\tau$ following the 90° pulse, the magnetizations P, Q rotate 180° around the y'-axis to thereby give a arrangement symmetrical to the state before the pulse is applied, with respect to the y'-axis (FIG. 3($c$)). In this arrangement, the nuclear magnetization P previously having an advanced phase ahead of Q now conversely has a delayed phase behind Q, so that both magnetizations will simultaneously reach the y'-axis, after the elapse of additional time $\tau$ (FIG. 3($d$)). Such relation holds with respect to nuclear magnetization in every region in the sample, so that all magnetizations concentrate on the y'-axis at this point of time, thereby producing a large NMR signal.

As has been described in the above, since the CPMG method first applies the 90° pulse in the direction of the x'-axis, and then applies the 180° pulse in the direction of the y'-axis, so that the nuclear magnetizations P, Q are inverted in the x'y'-plane as shown in FIG. 3($c$). Thereafter, the 180° pulse is applied in the direction of y'-axis at regular intervals, and inversion of the nuclear magnetization in the x'y'-plane occurs. Every time the inversion of the nuclear magnetization occurs, the compensation function works well. For example, even if positions of P, Q should shift above or below the x'y'-plane, typically due to (a) non-uniformity in the magnetic field, and (b) non-uniformity in intensity of the excitation pulse irradiated by the RF coil, the shift can be compensated by virtue of inversion of the nuclear magnetization in the x'y'-plane. It is presumed that an advantage of the CPMG method, such as being more likely to clearly show the correlation between the $T_2$ relaxation time constant and water content, is ascribable to the compensation function.

(ii) Step 106 (Measurement of $T_2$ Relaxation Time Constant)

Figure 4:
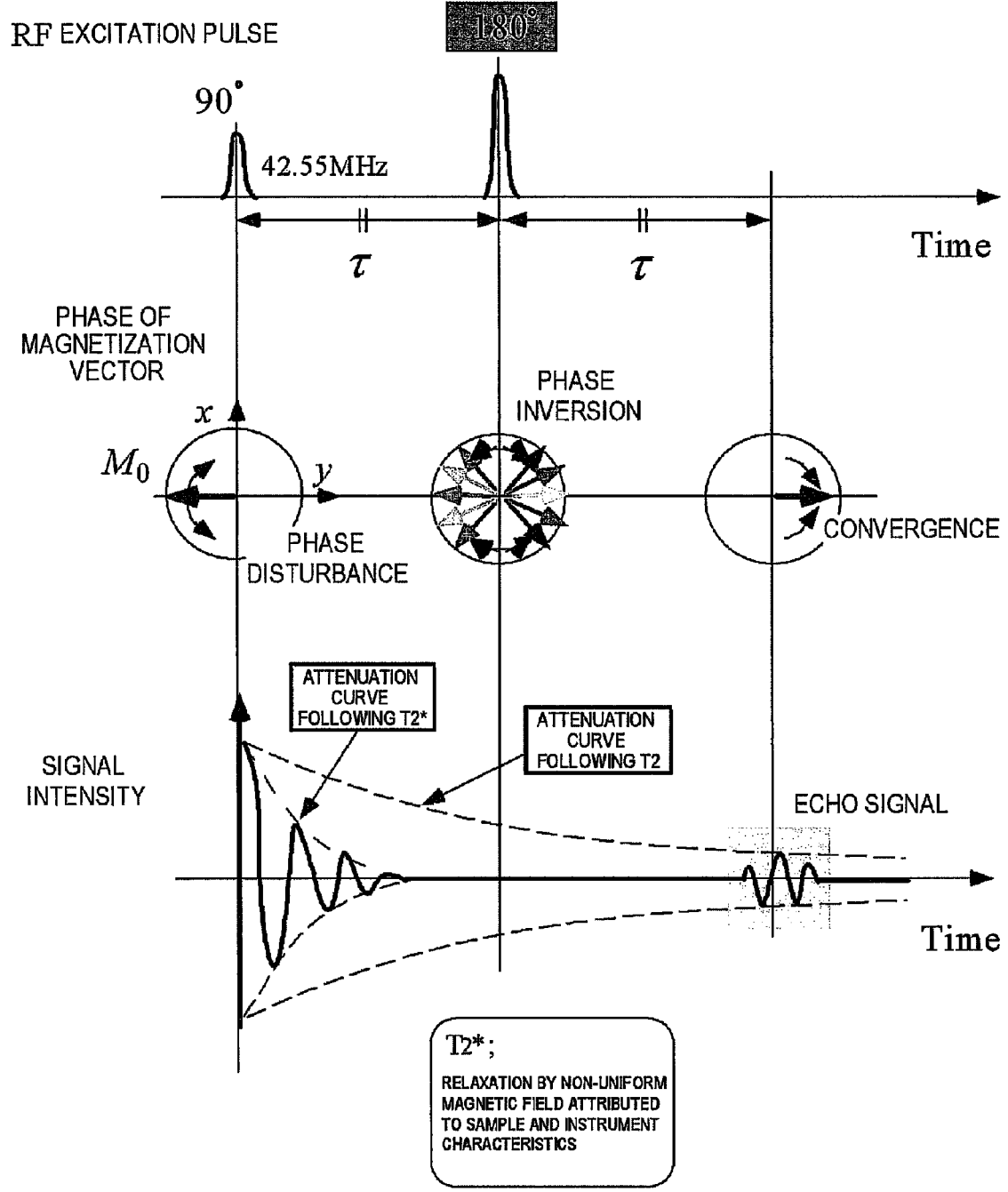
FIG. 4 is a drawing explaining a principle of measurement of $T_2$ relaxation time constant by the spin echo method.

The $T_2$ relaxation time constant can accurately be measured, by making use of the spin echo method (FIG. 4).

Resonantly excited magnetization vector $M_{-y}$ relaxes with time. Time-dependent changes in the magnetic resonance signal observed in this process attenuates according to some other time constant $T_2^*$ which cannot be expressed only by the spin-lattice relaxation time constant $T_1$ and the spin-spin relaxation time constant $T_2$. This behavior is shown in the bottom of FIG. 4, expressed as time changes in the signal intensity which starts immediately after the 90° excitation pulse. In general, intensity of thus actually measured magnetic resonance signal, expressed by broken lines, rapidly attenuates, and the time constant $T_2^*$ thereof appears as shorter than $T_2$. The reason why the actually observed attenuation signal attenuates more rapidly than the attenuation signal according to the $T_2$ relaxation is attributable to that a uniform magnetic field is not ensured over the entire portion of the signal, due to non-uniformity in the external static magnetic field formed by a static magnetic field magnet, and non-uniformity in the in-sample magnetic field due to magnetic properties or geometry of the sample. This sort of time changes in the magnetic resonance signal actually measured are referred to as free induction decay.

"Spin echo" is one of the methods of correcting the phase shifting caused by non-uniformity in the magnetic field as a result of sample- and instrument-related characteristics. The method is such that, after the elapse of time $\tau$ following the 90° excitation pulse, the 180° excitation pulse having doubled intensity is applied, so as to invert phase disturbance of magnetization vector M, which has been disturbing in progress on the x-y plane, and to make the phase converge after the elapse of time $2\tau$, and thereby an echo signal fitted to the $T_2$ attenuation curve can be obtained. This helps:

minimization of non-uniformity in the magnetic field as a result of sample- and instrument-related characteristics; and quantification of signal intensity (attenuation curve conforms to the $T_2$ relaxation time constant, independent of the instrument) and the like.

Intensity $S_{SE}$ of the echo signal obtained when the spin echo is adopted can be expressed by the equation (A) below, when TR>>TE holds.

Equation (A)

$$S_{SE} = A \cdot \rho(x, y, z) \cdot \left\{1 - \exp\left(-\frac{TR}{T_1}\right)\right\} \cdot \exp\left(-\frac{TE}{T_2}\right) \quad \text{(Equation 1)}$$

In this equation, $\rho$ expresses density distribution of a target nuclear species as a function of position (x,y,z), TR expresses repeating time of the 90° excitation pulse (approximately 100 ms to 10 s), TE expresses echo time ($2t$, approximately 1 ms to 100 ms), and A is a constant expressing detection sensitivity of the RF coil and characteristics of the instrument such as amplifier.

$T_2$ relaxation time constant can be determined based on the echo signal group fitted to the attenuation curve, and the equation (A) shown in the above.

In further detail, the 180° pulses are kept on irradiating at $2\tau$ intervals, and intensity of every even-numbered peak such as $2\tau$, $4\tau$, $6\tau$, ..., is obtained. The plurality of peak intensities gradually attenuate with time. Intensities of the plurality of echo signals thus attenuating with time are fitted to an exponential function, and the $T_2$ relaxation time constant can be determined based on the equation (A) in the above.

(iii) Step 108 (Measurement of Water Content)

In step 108, the water content is calculated based on the relaxation time constant. The water content in the sample and the $T_2$ relaxation time constant are positively correlated. As the water content increases, the $T_2$ relaxation time constant increases. Since this correlation differs by types, geometries and so forth of the sample, it is therefore preferable to preliminarily prepare an analytical curve with respect to samples equivalent to the sample to be measured but having known water contents. In other words, it is preferable to measure relations between the water content and the $T_2$ relaxation time constant using a plurality of standard samples of known water contents, to thereby preliminarily determine the analytical curve expressing the relation. By referring to thus prepared analytical curve, the water content of the sample can be calculated based on measured values of the $T_2$ relaxation time constant.

Method and theory of determining the water content from the relaxation time constant, and the reason why the CPMG method is suitable for the water content measurement, will be detailed below.

[Method and Theory of Determining Water Content Based on $T_2$ Relaxation Time Constant]

Polymer materials such as Nafion (registered trademark) membrane and the like have voids only as large as allowing water molecules to enter, attributable to geometry of the molecular chain. Water molecules includes those adsorbed to the polymer, and those freely moving in the space, wherein the $T_2$ relaxation time constants of the water molecules having constrained motion become short, and conversely the $T_2$ relaxation time constants of freely-movable water molecules become long.

Polymer materials swellable by absorbing water expand their voids as the amount of water contained therein increases. Therefore, gradual increase in the contained water allows water to adsorb first onto the polymer, and then to gradually fill the voids after the adsorption finished generally over the entire surface of the polymer. Therefore, dry polymer materials show short $T_2$ relaxation time constants because of having only water adsorbed onto the polymer, and the $T_2$ relaxation time constant elongates as the water content increases, because of increase in the amount of free water filling the space.

The $T_2$ relaxation time constant of the whole sample can be expressed by the equation below in a most simple form.

$$1/T_2(\text{whole})=(\text{amount of adsorbed water})/(T_2' \text{ of adsorbed water})+(\text{amount of free water})/(T_2'' \text{ of free water}) \quad (1)$$

The observer always measures the $T_2$ (whole). Since the $T_2$ (whole) increases as the amount of water filling the space increases, so that it is made possible to determine the content of water in the polymer based on the measured result of the $T_2$(whole).

[Reason why the CPMG Method Suitable for Measurement of Water Content]

Although the equation (1) was itemized by classifying the water into adsorbed water and free water, more detailed examination reveals presence of water susceptive to local non-uniformity in the static magnetic field, and water susceptive to uniform static magnetic field. Taking these facts into consideration, the equation (1) in the above can be written as:

$$1/T_2(\text{whole})=x/T_{2(a1)}+y/T_{2(a2)}+z/T_{2(b1)}+w/T_{2(b2)} \quad \text{equation (2)}$$

where, x: amount of adsorbed water susceptive to local non-uniformity in static magnetic field;

y: amount of adsorbed water susceptive to uniform static magnetic field;

z: amount of free water susceptive to local non-uniformity in static magnetic field;

w: amount of free water susceptive to uniform static magnetic field;

$T_{2(a1)}$: relaxation time constant of adsorbed water susceptive to local non-uniformity in static magnetic field;

$T_{2(a2)}$: relaxation time constant of adsorbed water susceptive to uniform static magnetic field;

$T_{2(b1)}$: relaxation time constant of free water susceptive to local non-uniformity in static magnetic field; and $T_{2(b2)}$: relaxation time constant of free water susceptive to uniform static magnetic field.

A reason for non-uniform magnetic field is ascribable to difference in magnetic susceptibility between water and the polymer membrane, and consequent difference in static magnetic field formed in bulk water and polymer, so that even application of the same magnetic field results in different intensities of magnetic fields penetrating the bulk water and penetrating the polymer, and distortion in the magnetic field occurs as a consequence.

As described in the above, water in the polymer exist in various states, and this raises a need of consideration from both aspects of classification, one from the viewpoint of the static magnetic field such as "places under uniform and non-uniform static magnetic fields", and the other from the view point of the state of water in polymer such that "whether water molecules reside in region of the polymer having wide voids, or adsorb on the wall surface".

In the equation (2) in the above, presence of the terms of $x/T_{2(a1)}$ and $z/T_{2(b1)}$ may be causative of difference in measurement accuracy of the relaxation time constant, due to presence or absence of compensation functions.

If the magnetic field changes from uniform to non-uniform, or from non-uniform to uniform due to migration of molecules by diffusion before the magnetization vector converges by the echo, an irreversible process generates in the spin, and Hahn's echo can no more converge the echo to the same state. On the other hand, CPMG has a compensation function of allowing the echo to return back to the same state, even if such exchanges between the uniformity and non-uniformity should occur. This is because the 180° excitation pulse capable of always allowing the phase to converge in the positive direction on the same y-axis is adopted, so as to avoid an irreversible phase dispersion process. The CPMG method, having such compensation function, is supposedly capable of accurately estimate value of the terms $x/T_{2(a1)}$ and $z/T_{2(b1)}$, and is considered as estimating correlation between the $T_2$ relaxation time constant and water content, more accurately as compared with Hahn's echo method.

Paragraphs below will explain an exemplary instrument realizing the method of locally measuring water, shown by the flow chart in FIG. 1.

FIRST EMBODIMENT

Figure 5:
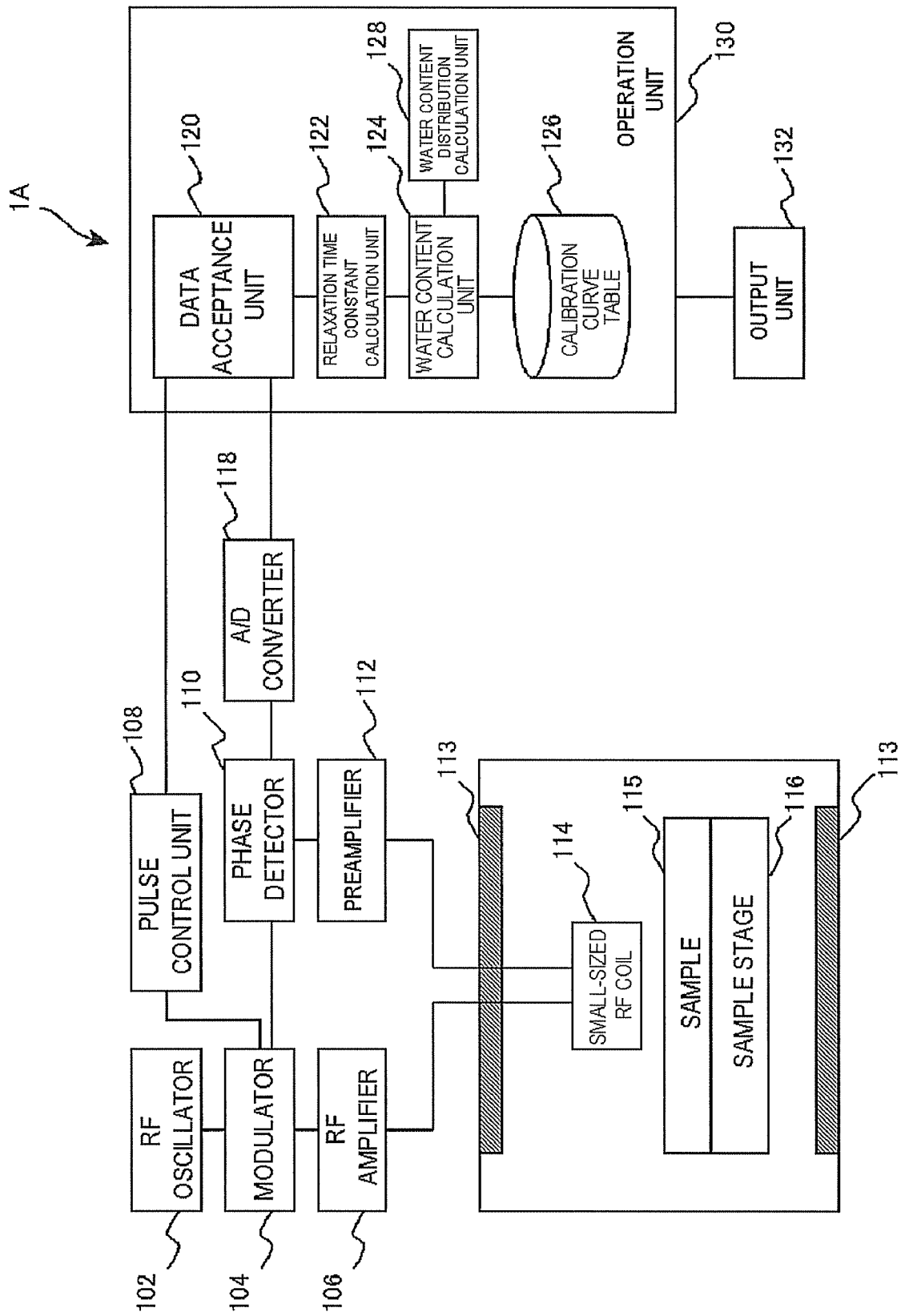
FIG. 5 is a drawing showing an overall configuration of a water content measurement instrument according to a first embodiment.

FIG. 5 is a drawing showing an overall configuration of a water content measurement instrument 1A according to this embodiment. The measurement instrument 1A is an instrument for locally measuring the water content at a specific position of a sample, and has a sample stage 116 on which a sample 115 is placed, a magnet 113 (static magnetic field application unit) applying a static magnetic field to the sample 115, a small-sized RF coil 114 disposed at a specific position over the sample 115, and an operation unit 130 calculating water content based on echo signals acquired by the small-sized RF coil 114.

The sample stage 116 is a stage on which the sample 115 is placed, and may be of a predetermined geometry and material.

The sample 115 is a target for measurement. The sample 115 may have various forms such as solid including membrane, block and the like, liquid, and gel such as agar, jelly-like substance and the like. A membrane-type substance is advantageous in view of stably obtaining results of measurement of local water content. The results of measurement will more stably be obtained, in particular by using a water-retaining membrane such as solid electrolyte membrane and the like.

The magnet 113 applies a static magnetic field to the sample 115. An excitation-use high frequency pulse is applied to the sample while applying the static magnetic field, and $T_2$ relaxation time constant is measured.

The small-sized RF coil 114 applies the excitation-use oscillating magnetic field to a specific position of the sample 115, and acquires the echo signals corresponded to the excitation-use oscillating magnetic field.

The small-sized RF coil 114 is preferably halved or smaller in size as compared with the whole size of the sample, and is particularly preferable to be downsized to $\frac{1}{10}$ or smaller. This way of size adjustment allows accurate measurement of local water content in the sample within a short time. The size of the sample may be expressed, for example, by a projected area of the sample placed elsewhere, wherein rapid and accurate measurement will be realized by adjusting the occupied area of the small-sized RF coil 114 to as small as preferably $\frac{1}{2}$ or below, and more preferably $\frac{1}{10}$ or below. The size of the small-sized RF coil 114 is preferably adjusted to not larger than, for example, 10 mm in diameter.

Figure 6:
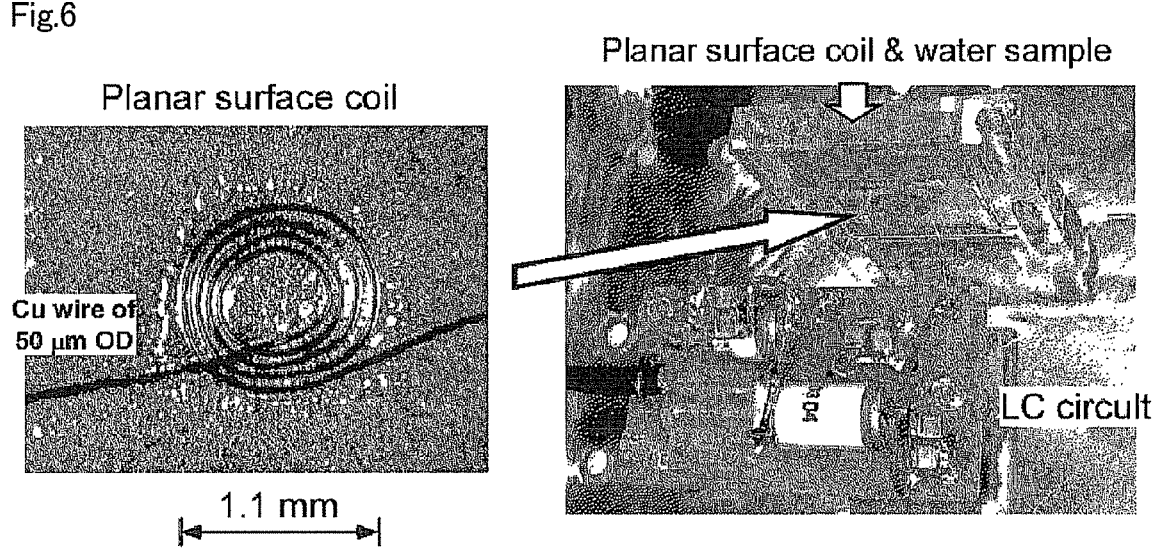
FIG. 6 is a drawing showing an exemplary small-sized RF coil.

The small-sized RF coil 114 applicable herein may be such as shown in FIG. 6. Use of the illustrated planar coil enables limitation of measurement area for local measurement. The measurement area covered by this sort of spiral coil is approximately as wide as the diameter of the coil, and approximately as deep as the radius of the coil. Unlike the general solenoid coil, this coil has a flat geometry, and can acquire NMR signals simply by placing it on the surface of the planar sample, as shown on the right of FIG. 6. Although the planar spiral coil was used in the above-described example, those having various geometries are adoptable without being limited thereto. For example, a planar 8-figure coil and the like is also adoptable. The 8-figure coil contains two spiral coil portions right-handed and left-handed. In contrast to the spiral coil having a sensitivity in the axial direction of the wound coil, the 8-figure coil can detect fluctuation in the magnetic field in parallel with the plane of two wound spiral coil portions.

A single, or a plurality of small-sized RF coils 114 may be used. Use of a plurality of coils enables measurement of water content distribution in the sample 115. In this case, two-dimensional arrangement of the coils over the surface of the sample 115 allows determination of two-dimensional water content distribution over the sample surface. Three-dimensional arrangement of the coils in the sample 115 allows determination of three-dimensional water content distribution in the sample.

The oscillating magnetic field (excitation-use oscillating magnetic field) applied by the small-sized RF coil 114 is produced by cooperation of an RF oscillator 102, a modulator 104, an RF amplifier 106, a pulse control unit 108 and the small-sized RF coil 114. More specifically, the excitation-use high frequency RF generated by the RF oscillator 102 is modulated by the modulator 104, while being controlled by the pulse control unit 108, and given in a pulse form. Thus-generated RF pulse is amplified by the RF amplifier 106, and then sent to the small-sized RF coil 114. The small-sized RF coil 114 applies the RF pulse to a specific position of the sample placed on the sample stage 116. An echo signal of the applied RF pulse is detected by the small-sized RF coil 114. The echo signal is amplified by a preamplifier 112, and then sent to a phase detector 110. The phase detector 110 detects the echo signal, and sends it to an A/D converter 118. The A/D converter 118 carries out A/D conversion of the echo signal, and sends it to the operation unit 130.

Figure 7:
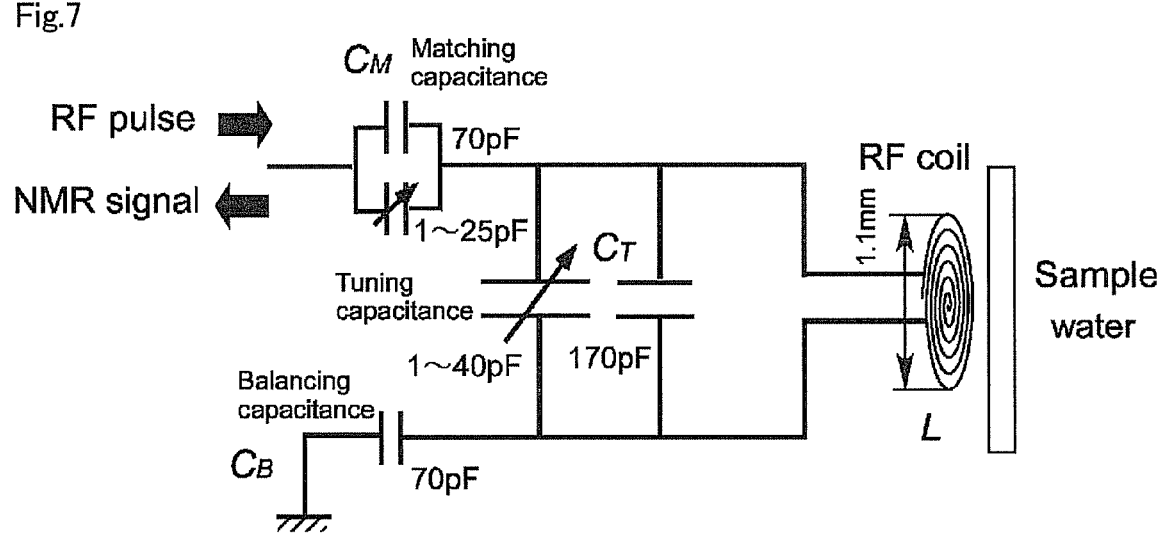
FIG. 7 is a drawing showing an exemplary LC circuit applying the excitation-use high frequency pulse and detecting the echo signal.

Application of the excitation-use high frequency pulse and detection of the echo signal described in the above can be realized by an LC circuit containing the small-sized coil. FIG. 7 is a drawing showing one example of such LC circuit. The coil portion (inductance portion) of the resonant circuit is composed of the small-sized RF coil as described in the above. The nuclear magnetic resonance (NMR) method can measure density of atoms and spin relaxation time constant, by detecting, as the NMR signals, motion of nuclear magnetization caused by spin resonance phenomenon of nuclei of atoms placed in the magnetic field. The spin resonance frequency in an 1-Tesla magnetic field is approximately 43 MHz (the frequency band is called radio frequency), and the LC resonant circuit as shown in FIG. 7 is used for detecting the frequency band in a highly-sensitive and selective manner.

The excitation-use high frequency pulse applied by the small-sized RF coil 114 to the sample 115 may be a pulse sequence typically composed of:

(a) a 90° pulse, and (b) "n" 180° pulses which start after the elapse of time $\tau$ following the pulse (a), applied at time $2\tau$ intervals.

For the purpose of clearly understanding correlations between the $T_2$ relaxation time constant and water content of the sample, it is essential to optimize the way of applying the oscillating magnetic field. Adoption of the above-described pattern helps clear understanding of correlations between the $T_2$ relaxation time constant and water content of the sample.

Adoption of a pulse sequence having the 90° pulse in the first phase, and "n" 180° pulses in the second phase shifted 90° from the first phase helps stable acquisition of clear correlations between the $T_2$ relaxation time constant and water content of the sample.

Use of the small-sized RF coil 114 may sometimes make it difficult to adjust excitation pulse intensity of the above-described (a) and (b). For example, the degree of excitation may differ between the center portion and the circumferential portion of a region to be measured, which is a region surrounded by the small-sized RF coil 114, so that it sometimes becomes difficult to excite the entire region so as to attain a uniform angle of excitation, in other words, so as to attain a constant intensity ratio of the excited magnetic field in (a) and (b). Any variations in the ratio of excitation angle in (a) and (b) makes accurate $T_2$ measurement difficult.

In this case, the pulse control unit 108 is configured so as to execute, in addition to the above-described pulse sequence, another sequence added with a step of applying 180° pulses, time i earlier than the 900 pulse (a). By comparing behaviors of attenuation curves of the 1800 pulses (b) corresponded to two these sequences, it is made possible to judge whether the excitation pulse intensities of the 900 pulse (a) and the 1800 pulses (b) are correct or not. As a consequence, any abnormality can be detected before the measurement, even if the excitation pulse intensity causes misalignment due to abnormalities in the instrument or the like, and thereby the measurement values can add exactness.

A configuration of the instrument has been explained in the above. A process block of the echo signal will be explained in the next.

The operation unit 130 calculates the $T_2$ relaxation time constant from intensity of the echo signal, and further calculates the water content at the specific position of the sample, based on thus calculated $T_2$ relaxation time constant.

Inside the operation unit 130, first an echo signal is acquired by a data acceptance unit 120, and the $T_2$ relaxation time constant is then calculated by a relaxation time constant calculation unit 122.

Once the $T_2$ relaxation time constant is calculated, the data thereof is sent to a water content calculation unit 124. The water content calculation unit 124 makes an access to a calibration curve table (storage unit) 126, and acquires a calibration curve data corresponded to the sample. The calibration curve table 126 has, as being stored therein by types of the sample, calibration curve data expressing correlations between water contents of the samples and the $T_2$ relaxation time constants.

The water content calculation unit 124 calculates water content of the sample, using thus-acquired calibration curve data and thus calculated $T_2$ relaxation time constant. The calculated water content is presented by the output unit 132 to the user. Modes of presentation may have various forms, and are not specifically limited, allowing outputs on displays, through printers, into files, and so forth.

In this embodiment, a plurality of small-sized RF coils 114 are disposed in the sample, on the surface of the sample, or in the vicinity of the sample. They are configured so as to apply the excitation-use oscillating magnetic field to a plurality of positions of the sample, and so as to acquire the echo signals corresponded thereto. A water content distribution calculation unit 128 calculates a water content distribution in the sample, based on the water contents measured at the plurality of positions of the sample. The output unit 132 outputs the water content distribution.

In the above-described instrument, the excitation-use high frequency pulse used herein is preferably those according to the CPMG method. This configuration allows stable acquisition of the correlation between the $T_2$ relaxation time constant and water content of the sample.

SECOND EMBODIMENT

Figure 8:
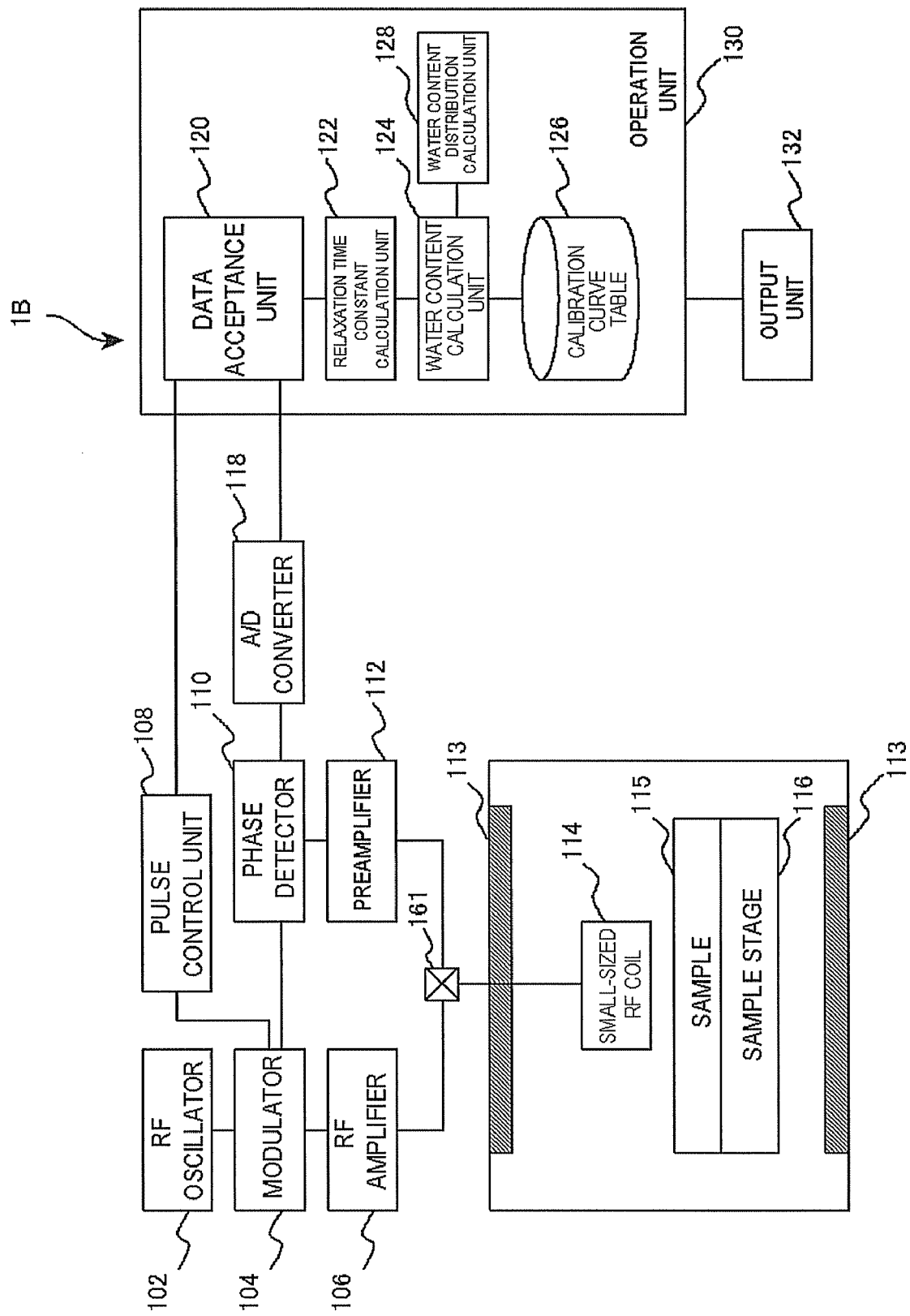
FIG. 8 is a drawing showing an overall configuration of a measurement instrument according to a second embodiment.

This embodiment relates to another example of the water content measurement instrument. FIG. 8 is a drawing showing a configuration of the water content measurement instrument according to this embodiment.

Basic configuration of a measurement instrument 1B shown in FIG. 8 is similar to that of the measurement instrument 1A shown in the first embodiment (FIG. 5), except that further having a switching unit 161.

The switching unit 161 is provided at a branching portion to which the small-sized RF coil 114, an RF signal generation unit and an echo signal detection unit are connected.

The RF signal generation unit is composed of the RF oscillator 102, a modulator 104 and the RF amplifier 106, and produces an RF signal allowing the small-sized RF coil 114 to generate the excitation-use oscillating magnetic field. The echo signal detection unit is composed of the preamplifier 112, the phase detector 110 and the A/D converter 118, detects the echo signal acquired by the small-sized RF coil 114, and sends the echo signal to the operation unit 130.

The switching unit 161 has a function of changing over:
a first state having the small-sized RF coil 114 and the RF signal generation unit (RF amplifier 106) connected with each other; and
a second state having the small-sized RF coil 114 and the echo signal detection unit (phase detector 110) connected with each other.

The switching unit 161 plays a role of a "send/receive change-over switch". Its role is to protect the preamplifier 112 in the receiving system by disconnecting it, when the excited pulse amplified by an RF power amplifier is transmitted to the small-sized RF coil 114, so as to protect it from large voltage, and also to isolate the preamplifier 112 in the receiving system so as to prevent noise emitted by amplification-use large transistors leaked from the RF amplifier 106 from being transmitted thereto, when the NMR signal is received after the excitation. Measurement using the small-sized RF coil 114 handles extremely weak signal, so that the switching unit 161 is required for the reasons described in the next. On the other hand, as for any large measurement system using no small-sized RF coil 114, "crossed diodes" are good enough to cope with this problem. The "crossed diodes" are diodes which turns on when applied with voltage of a predetermined value or above, and turns off if the voltage is lower than the predetermined value.

The reason why the "send/receive change-over switch", or the switching unit 161, is necessary when the small-sized RF coil 114 is used is as follows.

(i) Sample volume detectable by the small-sized coil of this measurement instrument is smaller than that detectable by a large-sized coil. The detectable sample volume is approximately (inside area of the coil×depth equivalent to radius of the coil). For the purpose of measuring extremely weak NMR signals which attenuate in proportion to the volume while ensuring low noise and high sensitivity, it is necessary, in the transmission system, to shut off noise leaked from large amplifying transistors of the RF amplifier 106. In the receiving system, it is necessary to use a high-sensitivity preamplifier 112. When the high-sensitivity preamplifier 112 is used, the preamplifier 112 must be disconnected so as to protect it from a large-voltage excitation pulse transmitted to the small-sized coil during transmission.

(ii) When nuclear magnetization is excited in the sample mass, it is necessary to excite the nuclear magnetization at an appropriate excitation pulse power, and more specifically, so as to adjust the ratio of intensities of the 90° pulse and the 180° pulses to 1:2. Any failure in appropriately adjusting the excitation pulse power will be unsuccessful in obtaining a target pulse sequence of the CPMG method, so that the measured $T_2$(CPMG) values degrades the reliability, and thereby the data will have variation. This phenomenon distinctively appears when the send/receive change-over switching of the small-sized coil is conducted using the conventional crossed diodes. Loss at the crossed diodes is negligible for large-sized coils having an extremely large excitation pulse intensity, whereas the loss at the crossed diodes is not negligible for the small-sized coils, because the excitation pulse intensity is smaller than that of large-sized coils. It is therefore necessary to provide the "send/receive change-over switch" causing only a minimum loss, in view of achieving an appropriate excitation pulse intensity.

Provision of the switching unit 161 at the branching portion can reduce the loss of excitation-use high frequency pulse signal applied from the small-sized RF coil 114 to the sample 115, and as a consequence, can accurately control the pulse angle of the 90° pulse and the 180° pulses. Accurate control of the pulse angle is one of important technical subjects in view of exactly obtaining the compensation effect in the pulse echo method, and this embodiment solves this subject by provision of the switching unit 161.

As the RF detection coil for local measurement is micronized, noise reduction in the NMR receiving process adds importance, in view of ensuring probability of the measurement. Noises possibly entering the preamplifier 112 in the receiving process of the NMR signal is largely contributed by the transmission system of RF wave, and also by "leakage RF wave" from the RF amplifier 106 amplifying the excitation-use pulse, and "noise emitted from large-current amplifier".

In the process of receiving the NMR signals, it is necessary to exactly shut off the excitation wave sent from the transmission side using the switching unit 161, so as to receive the NMR signals under low noise. This embodiment solves also this problem by provision of the switching unit 161.

Figure 9:
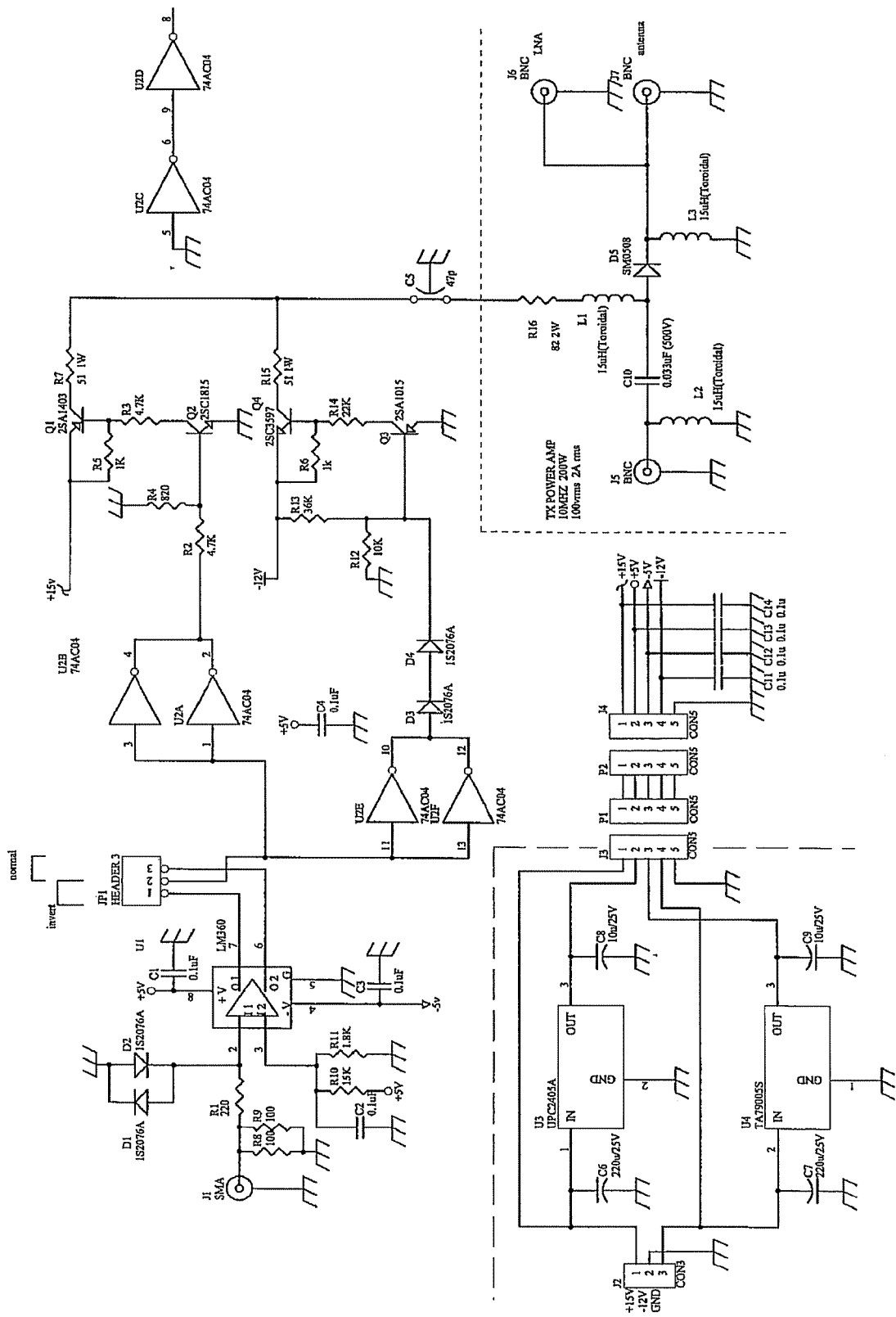
FIG. 9 is a drawing showing a configuration of a switching unit of the measurement instrument according to the second embodiment.

Various configurations may be applicable to the switching unit 161. FIG. 9 is a circuit diagram showing an exemplary configuration of the switching unit 161.

THIRD EMBODIMENT

Figure 10:
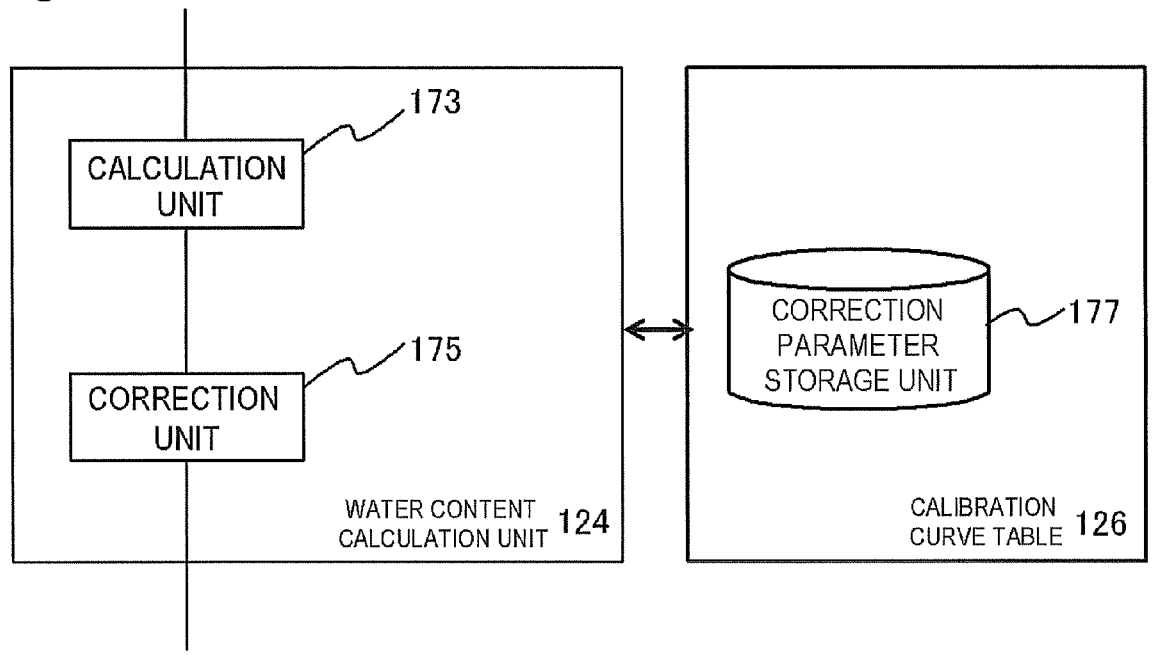
FIG. 10 is a block diagram detailing a measurement instrument according to a third embodiment.

This embodiment relates to another example of a method of calculating water content in the water content calculation unit 124 of the measurement instruments 1A, 1B described in the foregoing embodiments. FIG. 10 is a drawing showing a configuration of water content calculation unit 124 and the calibration curve table 126 in this embodiment.

As shown in FIG. 10, the water content calculation unit 124 has a calculation unit 173 calculating water content of the sample, and a correction unit 175 correcting the value calculated by the calculation unit 173, corresponding to the size of the small-sized RF coil 114. The calibration curve table 126 has a correction parameter storage unit 177 having stored therein correction parameters or correction equations relevant to correction carried out in the correction unit 175.

In the calculation unit 173, the $T_2$ relaxation time constant is calculated based on the echo signal detected by the small-sized RF coil 114, wherein in this embodiment, the measurement value may be shifted from that obtained in measurement using large solenoid coils or the like, due to smallness of the small-sized RF coil 114 applying the excited magnetic field.

In this case, the water content can be corrected in the correction unit 175 as the occasion demands. The correction parameter storage unit 177 has stored therein the correction parameters and methods of correction corresponding to the size of the small-sized RF coil 114, so that the correction unit 175 carries out the correction after acquiring the information from the correction parameter storage unit 177.

Use of the small-sized RF coil 114 basically yields measurement values equivalent to those obtained by using RF coils larger than the sample, but as described later in Examples, downsizing of the RF coil tends to cause difference in the degree of excitation of the sample, and generally raises factors causative of errors in the measurement values, such as non-uniformity in the magnetic field, and lowering in SN ratio and the like. In contrast to this, arrangement of the small-sized RF coil and adoption of a configuration having the switching unit provided therein, for example, can exclude the above-described factors, and can reduce influences of size of RF coil.

However, when the small-sized RF coil 114 is extremely micronized, the influence of size of RF coil may sometimes appear on the measurement values. The present inventors investigated into the influence, and made clear that the measurement values obtained by using the small-sized RF coil 114 can be converted into correct values using a predetermined constant. The conversion relates to an embodiment of multiplication by a predetermined constant, or an embodiment of adding a predetermined constant, allowing selection depending typically on properties of the sample. Correct measurement value unaffected by the size can be obtained by preliminarily determining the constant through preliminary experiments using the sample to be measured.

Reasons why the extreme micronization of the small-sized RF coil 114 may sometimes affect the measurement values are as follows.

In large-sized cylindrical coils, insertion of the sample inside the coil allows irradiation of the excitation-use oscillating magnetic field over the entire sample, so as to excite magnetization in a uniform, or almost uniform manner. As for the large-sized cylindrical coils, the coils are originally designed and manufactured so as to ensure uniform irradiation.

On the other hand, the small-sized RF coil 114 cannot uniformly excite the entire sample, because the coil is smaller than the sample. The portion at around the center of the coil is most strongly affected by the oscillating magnetic field, whereas the excited pulse intensity by the oscillating magnetic field decreases as the position is more distant therefrom.

The NMR signal emitted under such non-uniform excitation may contain magnetization components having various angle of excitation, sometimes showing phases of magnetization not aligned in the same direction. For this reason, the NMR signal received by the coil as a sum of these components may appear different from that obtained under uniform excitation. Features different from those obtained under uniform excitation typically relate to that the echo peaks do not look like laterally-symmetric, well-shaped mountain peaks, and that maximum peak positions thereof shift in the earlier or later direction on the time axis.

Calculation of the $T_2$(CMPG) by the CPMG method from such "NMR signals emitted from the non-uniformly excited pulse" may sometimes result in values different from those obtained by the large-sized coils under uniform excitation.

FOURTH EMBODIMENT

Figure 11:
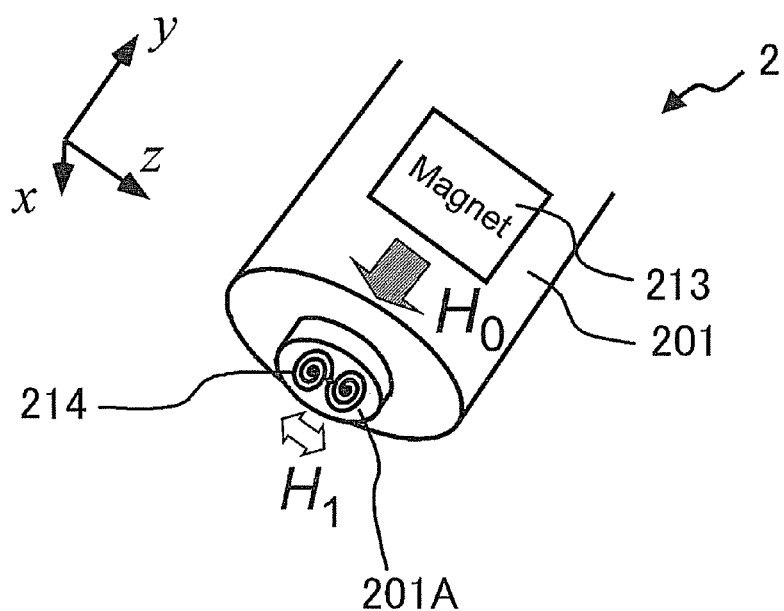
FIG. 11 is a drawing showing an essential portion of a measurement instrument according to a fourth embodiment.

In a measurement instrument 2 according to this embodiment, as shown in FIG. 11, a magnet (static magnetic field application unit) 213 and a small-sized RF coil 214 are attached to a support 210. Other aspects are same as those in the foregoing embodiments.

The magnet 213 is a small-sized magnet smaller than the magnet 113 of the measurement instruments 1A, 1B in the foregoing embodiments. In the foregoing embodiments, the magnet 113 applied the static magnetic field over the entire sample 115, whereas in this embodiment, the magnet 213 is used to apply the static magnetic field to a specific position of the sample 115.

The support 201 is a stick-like enclosure.

At the center of the end face of the end portion of the support 201, a projection 201A is formed.

In the support 201, a magnet 213 is housed. The static magnetic field $H_0$ from the magnet 213 is aligned in the same direction with the center axis of the support 201.

Figure 12:
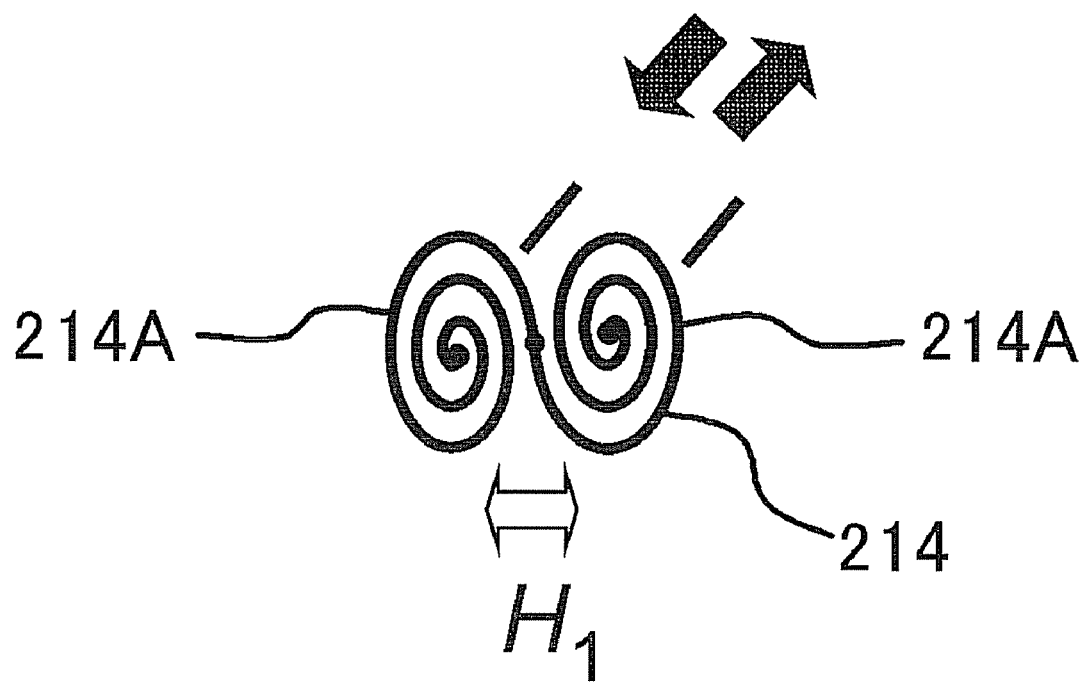
FIG. 12 is a drawing showing a small-sized RF coil of a measurement instrument according to the fourth embodiment.

In this case, the excitation-use oscillating magnetic field $H_1$ is necessarily applied in the direction perpendicular to the center axis of the support 201, so that so-called "8-figure-type", or "butterfly-type", small-sized RF coil 214 having two spiral (ring-form) coil portions 214A linked with each other, as shown in FIG. 12, is used.

A pair of coil portions 214A is disposed in the direction substantially perpendicular to the direction of the static magnetic field, wherein one coil portion 214A is wound right-handed, and the other coil portion 214A is wound left-handed.

Thus configured small-sized RF coil 214 is fixed on the surface of the projection formed on the end face of the end portion of the support 201.

In this configuration, the direction of static magnetic field $H_0$ and the direction of the excitation-use oscillating magnetic field $H_1$ of the small-sized RF coil 214 cross perpendicular to each other, allowing receive of the NMR signal.

Thus configured measurement instrument 2 can be used simply by bringing the small-sized RF coil 214, attached to the end portion of the support 201, into contact with the sample.

In this embodiment, the small-sized magnet 213 applying the static magnetic field $H_0$ is attached to the support 201, so that it is no more necessary to use the large-sized magnet 113 as shown in the foregoing embodiments, allowing downsizing of the measurement instrument 2.

In addition, the support 201 has a stick form, and thereby allows the user to carry out the measurement simply by holding the support 201 and bringing the end portion thereof into contact with the sample, so that the operability of the measurement instrument can be improved.

FIFTH EMBODIMENT

The fifth embodiment will be explained referring to FIGS. 13, 14.

This embodiment relates to a fuel cell system 3 provided with the measurement instrument 1A according to the first embodiment.

Figure 13:
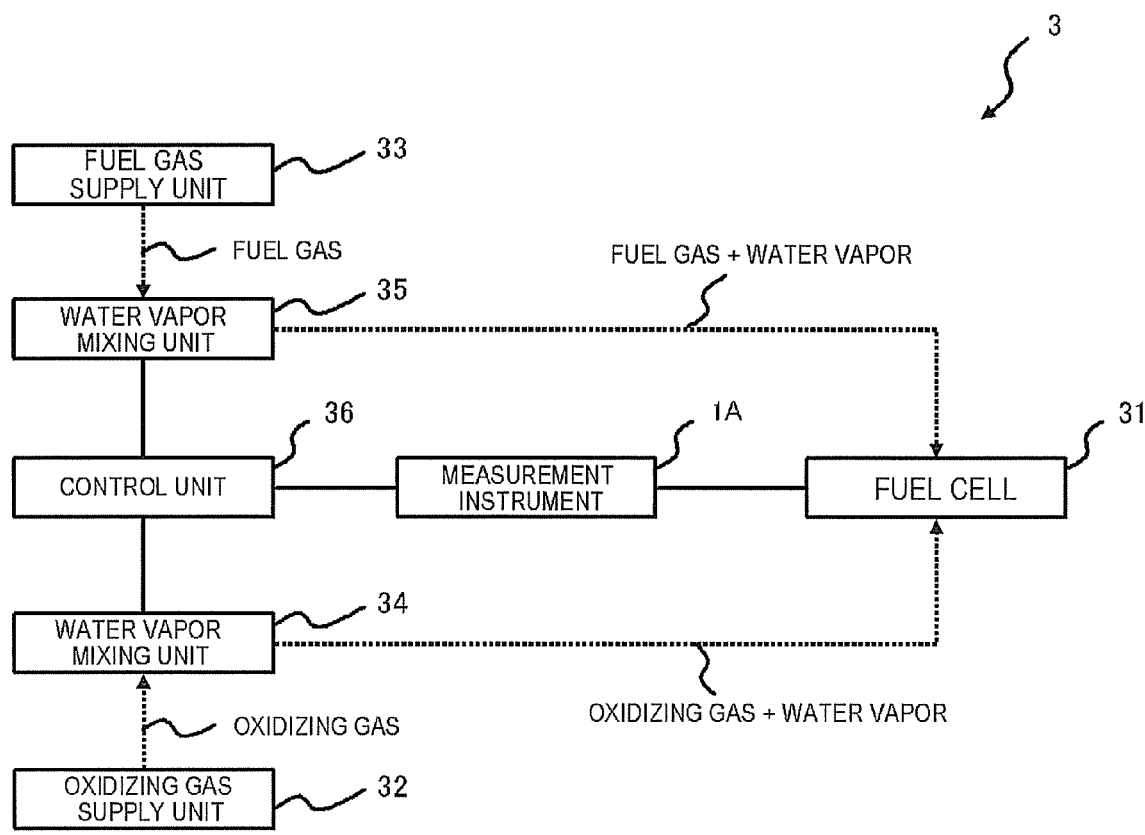
FIG. 13 is a block diagram showing a fuel cell system according to a fifth embodiment.

As shown in FIG. 13, the fuel cell system 3 has the measurement instrument 1A, a fuel cell 31, an oxidizing gas supply unit 32 supplying an oxidizing gas (oxygen, air, and the like) to the fuel cell 31, a fuel gas supply unit 33 supplying a fuel gas (hydrogen gas or the like) to the fuel cell 31, a water vapor mixing units 34, 35 mixing water vapor with the oxidizing gas supplied from the oxidizing gas supply unit 32 to the fuel cell 31, and with the fuel gas supplied from the fuel gas supply unit 33 to the fuel cell 31, and a control unit 36.

Figure 14:
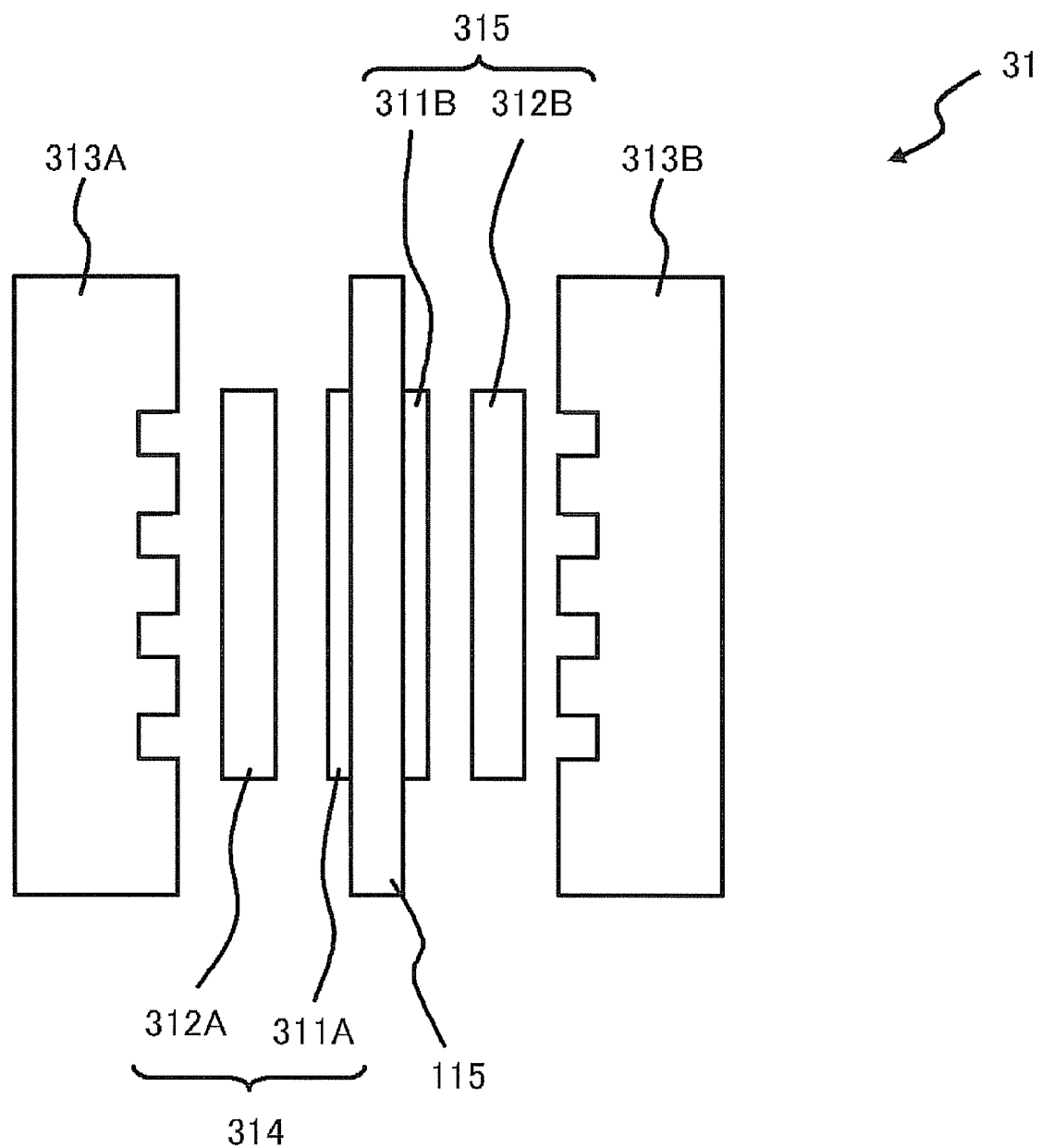
FIG. 14 is a drawing showing a structure of the fuel cell.

The fuel cell 31 has, as shown in FIG. 14, a polymer membrane (sample) 115, catalyst layers 311A, 311B provided on both sides of the polymer membrane 115, porous diffusion layers 312A, 312B and separators 313A, 313B.

The catalyst layer 311A and the diffusion layer 312A compose an anode electrode 314, and the catalyst layer 311B and the diffusion layer 312B compose a cathode electrode 315.

The separator 313A is supplied with the fuel gas, and has formed therein grooves serving as channels for the fuel gas.

Also, the separator 313B is supplied with the oxidizing gas, and has formed therein grooves serving as channels for the oxidizing gas.

The oxidizing gas supply unit 32 is a unit supplying the oxidizing gas to the fuel cell 31, and the fuel gas supply unit 33 is a unit supplying the fuel gas to the fuel cell 31.

Between the oxidizing gas supply unit 32 and the fuel cell 31, a water vapor mixing unit 34 is provided. The water vapor mixing unit 34 generates water vapor, and mixes the water vapor to the oxidizing gas supplied from the oxidizing gas supply unit 32 to the fuel cell 31. The oxidizing gas thus mixed with water vapor is supplied to the fuel cell 31.

Similarly, between the fuel gas supply unit 33 and the fuel cell 31, a water vapor mixing unit 35 is provided. The water vapor mixing unit 35 generates water vapor, and mixes the water vapor with the fuel gas supplied from the fuel gas supply unit 33 to the fuel cell 31. The fuel gas thus mixed with the water vapor is supplied to the fuel cell 31.

By mixing the water vapor with the oxidizing gas and with the fuel gas, the polymer membrane 115 of the fuel cell 31 is allowed to swell.

When water content of the polymer membrane 115 of the fuel cell 31 is measured, a plurality of small-sized RF coils 114 of the above-described measurement instrument 1A are brought into contact with the surface of the polymer membrane 115. The water content of the polymer membrane 115 is thus measured.

The control unit 36 is connected to the measurement instrument 1A and the water vapor mixing units 34, 35.

The control unit 36 acquires results of measurement of water content and water content distribution from the measurement instrument 1A, and controls the water vapor mixing units 34, 35, based on the results of measurement, so as to adjust the amount of water vapor generated by the water vapor mixing units 34, 35 and supplied to the fuel cell 31.

For example, during the power generating operation of the fuel cell 31, in parallel with migration of hydrogen ions generated on the anode electrode 314 side, water in the polymer membrane migrates from the anode electrode 314 side to the cathode electrode 315 side.

On the other hand, water is generated through a reaction between hydrogen ions and oxygen gas on the cathode electrode 315 side. The water content of the polymer membrane 115 may therefore become excessive, in particular on the cathode electrode 315 side thereof. Excessive water content may cause condensation of water in the channels of the separator 313B, may interfere flow of the oxidizing gas, and may degrade the power generation efficiency.

On the other hand, dryness of the polymer membrane 115 due to insufficient supply of water vapor to the polymer membrane 115 degrades the proton conductivity, and thereby degrades the power generation efficiency of the fuel cell 31. It is therefore not preferable to dry up the polymer membrane 115, and to lower the proton conductivity.

The control unit 36 then acquires water content distribution from the measurement instrument 1A, and judges whether the water content value in the acquired distribution falls in a predetermined range or not, that is, whether the polymer membrane 115 is in an adequately moistened state. If the water content was judged as exceeding the predetermined range, the control unit 36 sends a request to the water vapor mixing units 34, 35 so as to decrease the amount of water vapor to be generated.

One the other hand, if the water content value in the water content distribution acquired from the measurement instrument 1A was judged as being out of a predetermined range, and as being below the range, the control unit 36 sends a request to the water vapor mixing units 34, 35 so as to increase the amount of water vapor to be generated, and thereby prevents dryness of the polymer membrane 115.

In thus configured fuel cell system 3, water content of the polymer membrane 115 is measured by the measurement instrument 1A, and the water content of the polymer membrane 115 is adjusted to an appropriate level. As a consequence, the power generation efficiency of the fuel cell 31 can be improved.

It is also allowable to bring the small-sized RF coil 114 into contact with the surfaces of the polymer membrane 115 respectively on the anode electrode 314 side and on the cathode electrode 315 side, so as to find the water contents respectively in the surficial portion on the anode electrode 314 side and in the surficial portion on the cathode electrode 315 side, to thereby understand relations between the water content in the surficial portions of the individual electrodes 314, 315 and the power generation efficiency.

It is therefore made possible to understand that supply of water vapor from which of the anode electrode 314 side and the cathode electrode 315 side is more effective to the power generation efficiency.

Moreover, the fuel cell system 3 of this embodiment can provide useful data for searching causal factors of degradation in the power generation efficiency, possibly occurs when the fuel cell system 31 is operated for a long duration of time, from the viewpoint of "water content of the polymer membrane".

Although the amount of generation of water vapor in both of the water vapor mixing units 34, 35, and the amount of supply of water vapor to the fuel cell 31 were adjusted by the control unit 36 in this embodiment, the adjustment is not limited thereto, instead allowing adjustment of only the amount of generation of water vapor by the water vapor mixing unit 35, and the amount of supply of water vapor to the fuel cell 31, for example.

Further, the fuel cell system 3 in this embodiment was configured as having the measurement instrument 1A, wherein the configuration is not limited thereto, instead allowing adoption of any measurement instrument of the foregoing embodiments and a sixth embodiment described in the next.

SIXTH EMBODIMENT

Figure 27:
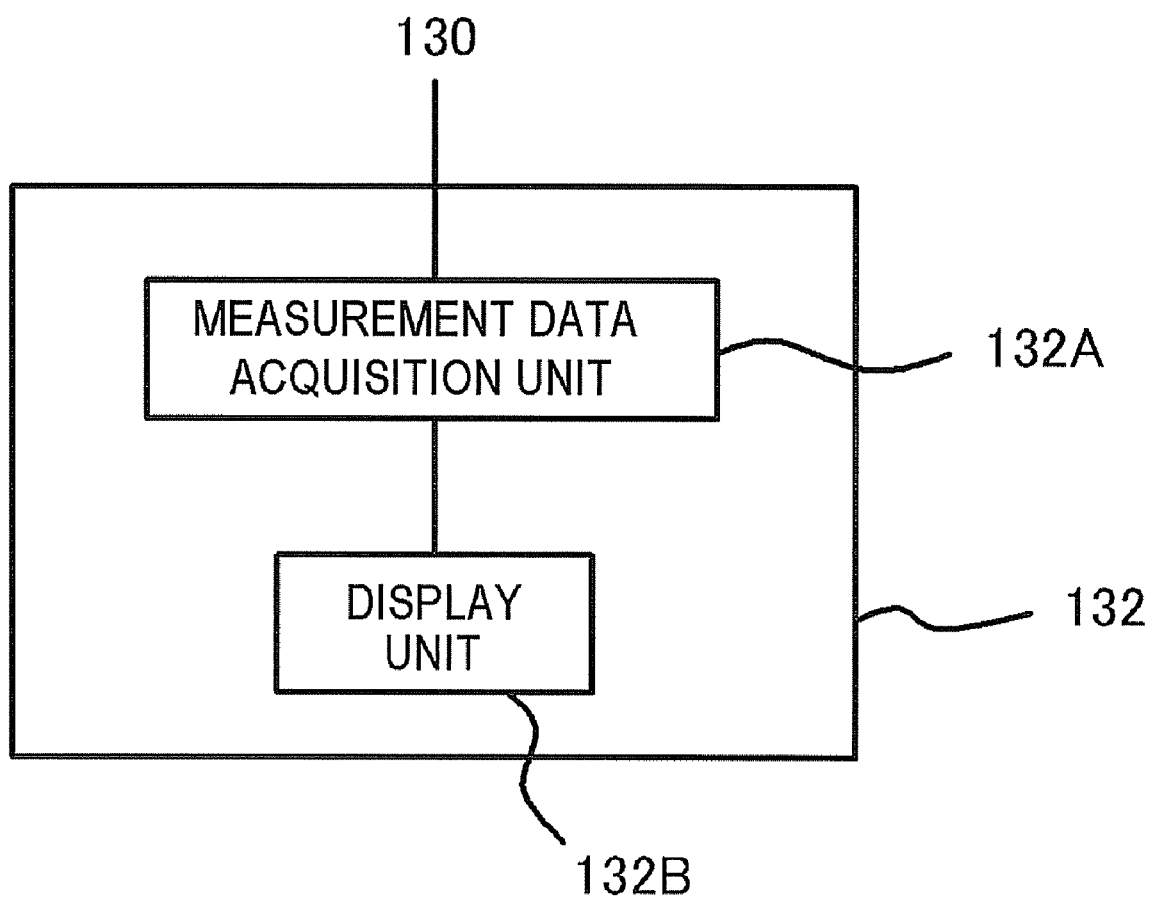
FIG. 27 is a block diagram of an output unit according to a sixth embodiment.

This embodiment will be explained referring to FIGS. 27, 28.

This embodiment shows another example of the output unit of the water content measurement instruments 1A, 1B, 2 in the foregoing embodiments.

Figure 28:
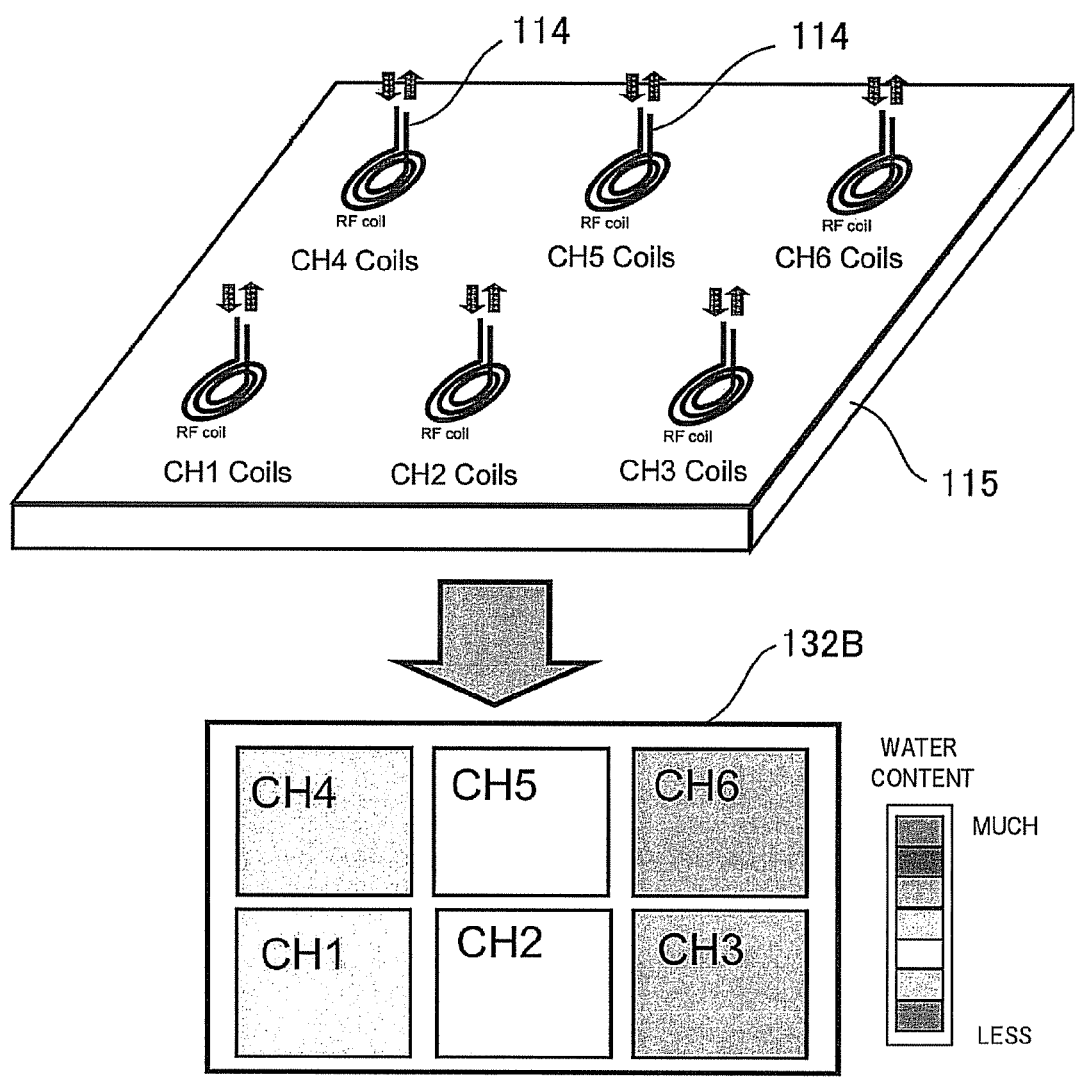
FIG. 28 is a drawing showing a display unit according to the sixth embodiment.

The output unit 132 has a measurement data acquisition unit 132A acquiring water contents for every measurement area of a plurality of small-sized RF coils 114 (FIG. 28 shows the small-sized RF coils 114, but the small-sized RF coils 214 also allowable), calculated by the water content calculation units 124, and a display unit 132B displaying the acquired water contents in partitioned regions on a single screen.

In the display unit 132B, the screen is divided into a plurality of regions as shown in FIG. 28, corresponding to the positions of arrangement of the small-sized RF coils 114. The individual regions are displayed in predetermined colors, corresponding to the water contents in the measurement regions of the individual small-sized RF coils 114.

By displaying colors corresponded to the water contents of the measurement regions of the individual small-sized RF coils 114, in the individual regions of the display unit 132B, relation between the measurement positions of the individual small-sized RF coils 114 and water content can be understood in an intuitive manner.

The measurement instrument will therefore be convenient-to-use for the user.

EXAMPLES

Referential Example

In the referential example, strong dependence of the $T_2$ relaxation time constant of the polymer membrane (sample) on the water content was confirmed.

[Configuration of Instrument]

The small-sized RF coil of the measurement instrument explained in the first embodiment was replaced with a standard-type solenoid coil (referred to as standard coil, hereinafter), and put into measurement.

The standard coil is 25 mm in diameter and 38 mm long, and is sufficiently larger than the polymer membrane to be measured.

This sort of standard coil can excite nuclear magnetization of the sample (polymer membrane) inserted therein, and can ensure high reliability in the measurement.

[Sample]

A polymer membrane of 500 μm thick and 15 mm×15 mm in size (from Asahi Glass Co., Ltd.) was used as the sample.

The polymer membrane was immersed in a 3% hydrogen peroxide solution kept at 80° C., and stirred for one hour. The polymer membrane was then immersed sequentially in a 1-N hydrochloric acid and ion-exchanged water in this order, and stirred respectively for one hour (standardization treatment).

The polymer membrane was then immersed in distilled water at room temperature, and stored.

[Moistening and Heating of Polymer Membrane]

Figure 15:
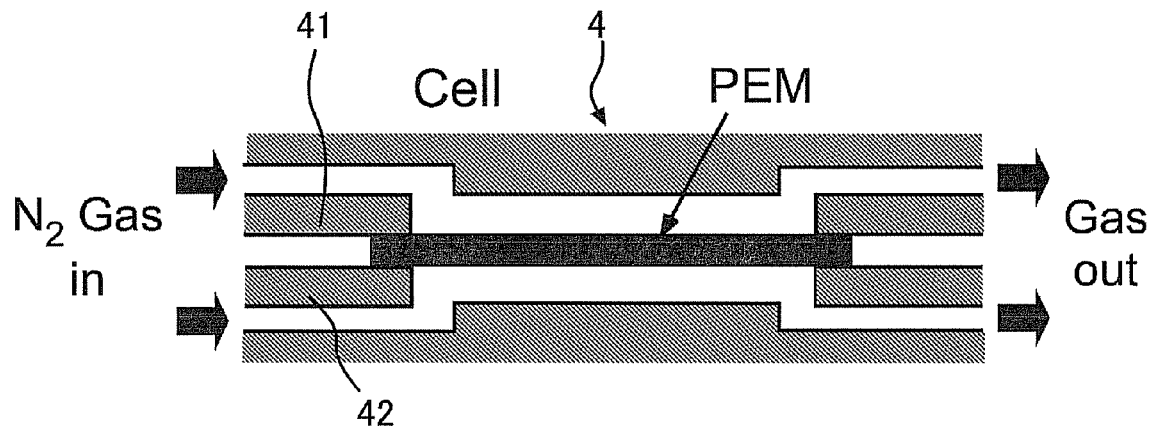
FIG. 15 is a schematic drawing showing a moistening/heating cell according to a referential example.

A moistening/heating cell 4 shown in FIG. 15 was fabricated, aimed at heating the polymer membrane to 75° C., and moistening it in an atmosphere having a predetermined water vapor concentration.

A temperature of the polymer membrane of 75° C. was adopted because the polymer membrane was intended for use in a fuel cell. The fuel cell is operated at 60 to 70° C.

In the moistening/heating cell 4 shown in FIG. 15, the polymer membrane is disposed as being held between an upper component 41 and a lower component 42 disposed in the cell.

On the surface of the polymer membrane held between the upper component 41 and the lower component 42, there are formed channels allowing therethrough flow of moistened nitrogen gas. Nine channels are formed in a 12.2 mm×12.0 mm region on the surface of the polymer membrane.

Both of width and depth of the individual channels are 1.0 mm, and pitch of the channels is 1.4 mm.

Flow rate of the moistened nitrogen gas is 50 ml/min.

The moistened nitrogen gas is prepared and introduced into the moistening/heating cell 4 as described below.

First, nitrogen gas is washed in a first bubbler at room temperature, and then in a second temperature-controlled bubbler, blown out through a porous glass plate having a pore size of 10 μm. This process can successfully produce the moistened nitrogen gas having a given concentration of water vapor.

The moistened nitrogen gas was introduced into the moistening/heating cell 4, while keeping all piping allowing the moistened nitrogen gas to flow therethrough at 77° C., so as to avoid condensation of the moistened nitrogen gas after being moistened.

Temperature control of the moistening/heating cell 4 was accomplished by allowing a liquid kept at 75° C. to flow through the cell, and temperature of the polymer membrane was adjusted to the same temperature with the moistening/heating cell 4.

In this way, the moistened nitrogen gas having a given water vapor concentration was introduced into the moistening/heating cell 4, and the steady state was kept for 4 hours or more. The polymer membrane having a given water content was obtained in this way.

[Measurement of Water Content of Polymer Membrane]

Figure 16:
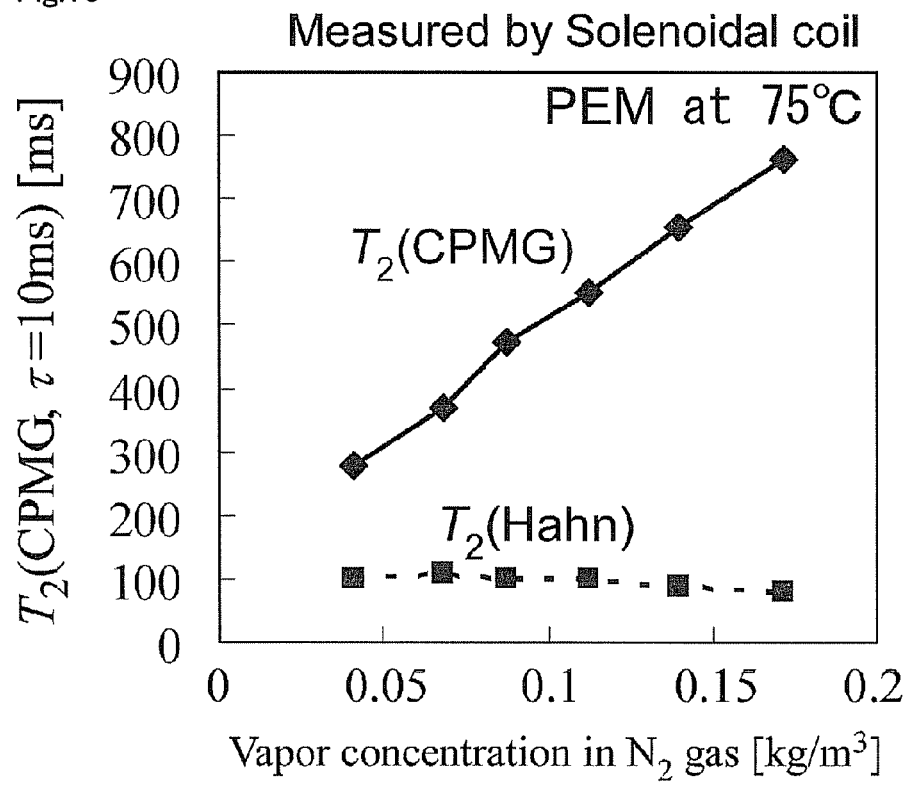
FIG. 16 is a drawing showing a relation between water vapor concentration of moistened nitrogen gas and $T_2$ relaxation time constant.

While varying water vapor concentration of the moistened nitrogen gas flowing through the moistening/heating cell 4, and at the individual water vapor concentrations, the $T_2$ relaxation time constants were measured using the above-described standard coil, results of which shown in FIG. 16. FIG. 16 shows results of the measurement adopting the CPMG method and Hahn's echo method, respectively.

Variation in the $T_2$ relaxation time constant (CPMG) obtained by the CPMG method was found to fall in the range from 18 ms to 26 ms.

Also, errors and fluctuation in the water vapor concentration are mainly ascribable to fluctuation in bubbler temperature. Fluctuation in the bubbler temperature ranges from −0.5° C. to +0.5° C., and correspondent fluctuation in the water vapor concentration is estimated as −2% to +2%.

It is found from FIG. 16 that the $T_2$ relaxation time constant (CPMG) obtained by the CPMG method increases almost proportional to increase in the water vapor concentration. For this reason, it is supposed that increase in the water vapor concentration increases the water content of the polymer membrane, and thereby increases water molecules freely movable in the polymer membrane.

It is therefore concluded that the water content in the polymer membrane can be calculated by measuring the $T_2$ relaxation time constant (CPMG) by the CPMG method.

On the other hand, when the $T_2$ relaxation time constant (Hahn) is measured by Hahn's echo method, the $T_2$ relaxation time constant (Hahn) obtained by the Hahn's echo method is found as being approximately constant, rather than being dependent on the water vapor concentration.

Example 1

Based on nuclear magnetic resonance (NMR) method, making use of (i) local measurement using a small-sized RF coil, and (ii) strong dependence of the $T_2$ relaxation time constant of the polymer membrane on the water content, it is made possible to locally measure the water content of the polymer membrane, within a short period of time with a high sensitivity. The process will be explained below, referring to the Example.

[Configuration of Instrument]

Using the measurement instrument configured as explained in the first embodiment, water content of the sample was locally measured. The instrument adopts the small-sized RF coil, and a multi-echo signal was measured using the CPMG method.

[Sample]

Flemion (registered trademark) of 500 µm in thickness and 16 mm×16 mm in size was used as the sample.

[Preliminary Experiments]

Figure 2:
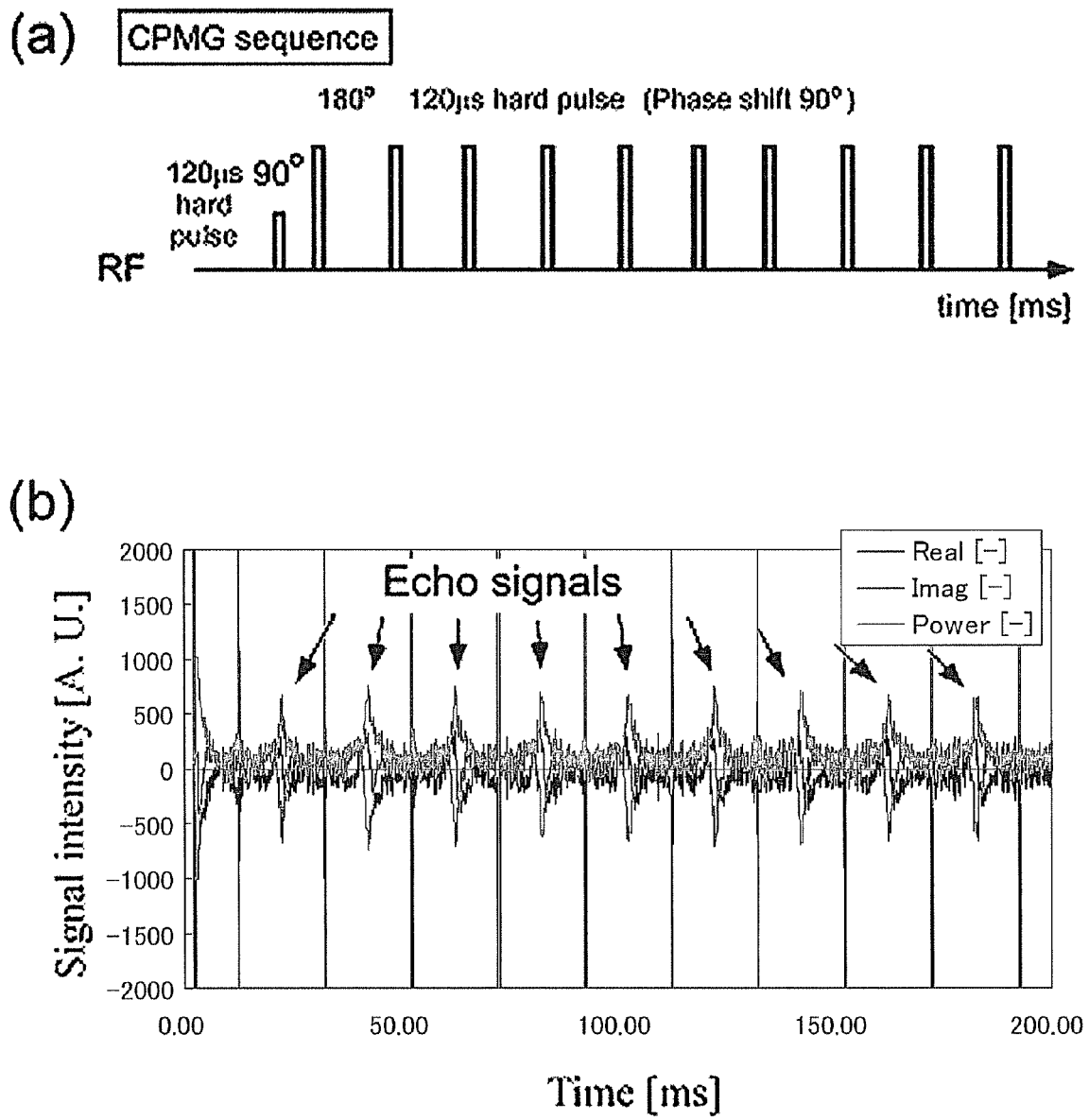
FIG. 2(a) is a drawing showing an exemplary pulse sequence in the CPMG method, and (b) is a drawing showing exemplary echo signals.

First, for the purpose of proving that NMR signals can adequately be obtained using the small-sized RF coil, multi-echo signal was measured using the CPMG method. In this process, a small-sized RF coil of 1.1 mm in diameter was used, and pure water was used as the sample. Results are shown in FIG. 2. It is found that the small-sized RF coil can appropriately irradiate 90°-180° excitations pulses, and $T_2$ relaxation time constant of the pure water sample are measured to a level equivalent to that obtained by a solenoid coil.

[Measurement of Water Content of Polymer Membrane]

Figure 17:
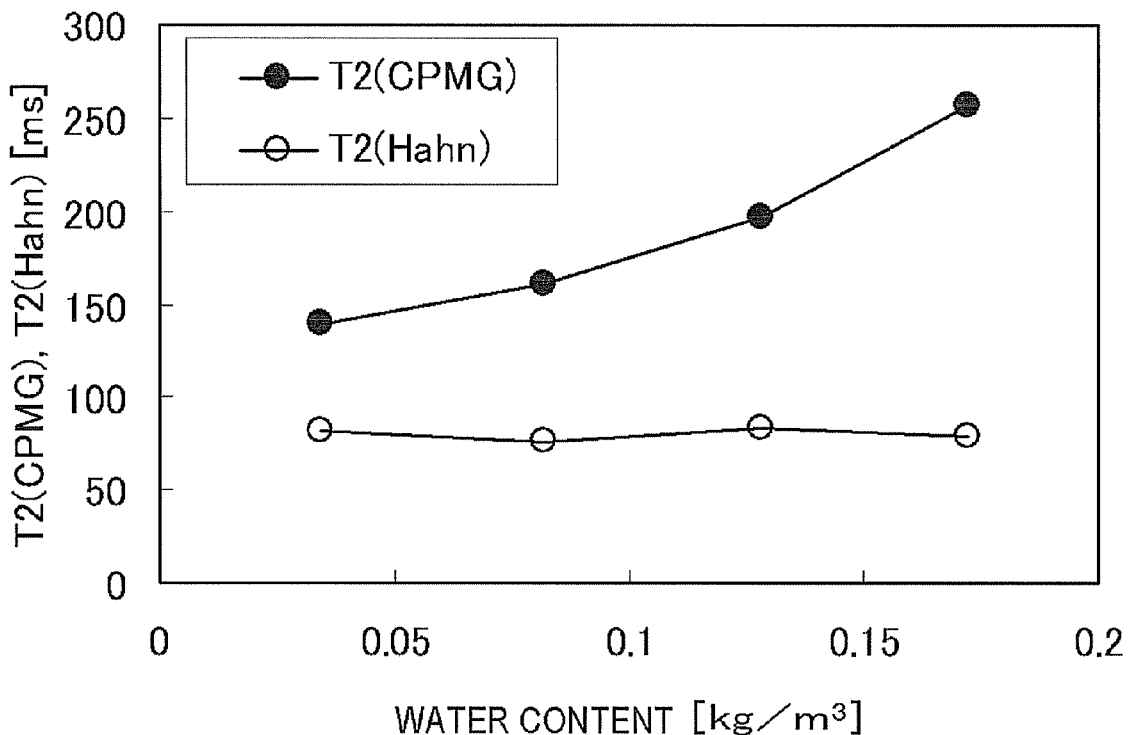
FIG. 17 is a drawing showing results of measurement of a multi-echo signal measured by the CPMG method in Example 1.

Using the above-described instrument, $T_2$ relaxation time constants were measured respectively by the CPMG method and Hahn's echo method, while varying water content of the polymer membranes. Results are shown in FIG. 17. Water vapor concentration plotted on the abscissa axis expresses water vapor concentration at around the polymer membrane, and the membrane has a water content keeping an equilibrium with the water vapor concentration. For this reason, the abscissa axis can be assumed as expressing water content of the polymer membrane. From this drawing, it is found that $T_2$ relaxation time constant determined by the CPMG method elongates as the water content of the membrane increases, whereas the $T_2$ relaxation time constant determined by Hahn s echo method was found to remain constant.

General MNR measurement adopts Hahn's echo method to obtain the echo signal, and then visualizes the signal intensity, so that the $T_2$ relaxation time constant (Hahn's echo) does not depend on water content of the membrane, showing no difference in contrast by the $T_2$ relaxation time constant (Hahn's echo), but is simply proportional to the water content, even if the water content distribution should include high concentration region and low concentration region. For this reason, measurement based on Hahn's echo method can give only a less sensitive method of measuring the water content.

On the contrary, the $T_2$ relaxation time constant (CPMG) in the CPMG method elongates as the water content increases, and shows a clear difference in the $T_2$ relaxation time constant (CPMG) between the high water content region and the low water content region. The water content can, therefore, be calculated by measuring the $T_2$ relaxation time constant by the CPMG method. Image measurement by the CPMG method also results in enhanced contrast, because of increasing effects of both of the water content and the $T_2$ relaxation time constant (CPMG).

As has been described in the above, the instrument and method adopted in this embodiment allows calculation of the water content, from both aspects of the amplitude of the NMR signal and the $T_2$ relaxation time constant, and acquisition of the multi-echo using the CPMG method allows measurement of water content of the polymer membrane with a high sensitivity. Measurement time in the CPMG method is one second or shorter, so that the measurement time of water content by this method is reduced to one second or shorter.

Example 2

In this Example, it was confirmed that use of the small-sized surface coil allows measurement of $T_2$(CPMG) to a level equivalent to that obtained by the standard coil. $T_2$(CPMG) was measured using aqueous copper sulfate solution stabilized over a duration of time as samples.

First, $T_2$(CPMG) was measured using aqueous copper sulfate solutions differed in the concentration. The samples used herein were aqueous copper sulfate solutions having concentrations of 0, 2.5, and 5.0 mmol/l. The $T_2$ relaxation time constant varies depending on these concentrations.

The sample was sealed into a container (inner size 15 mm×15 mm×gap 0.5 mm, thickness 0.12 mm). The small-sized surface coil was attached to the center of the sample container, keeping a distance between the coil and the aqueous solution of 0.15 mm, including a polyimide film of 30 µm thick. For comparison, a solenoid coil of 25 mm in diameter and 38 mm in length, sufficiently larger than the sample, and known to have an excellent irradiation uniformity of high frequency magnetic field was used as a standard solenoid coil (standard coil).

Figure 18:
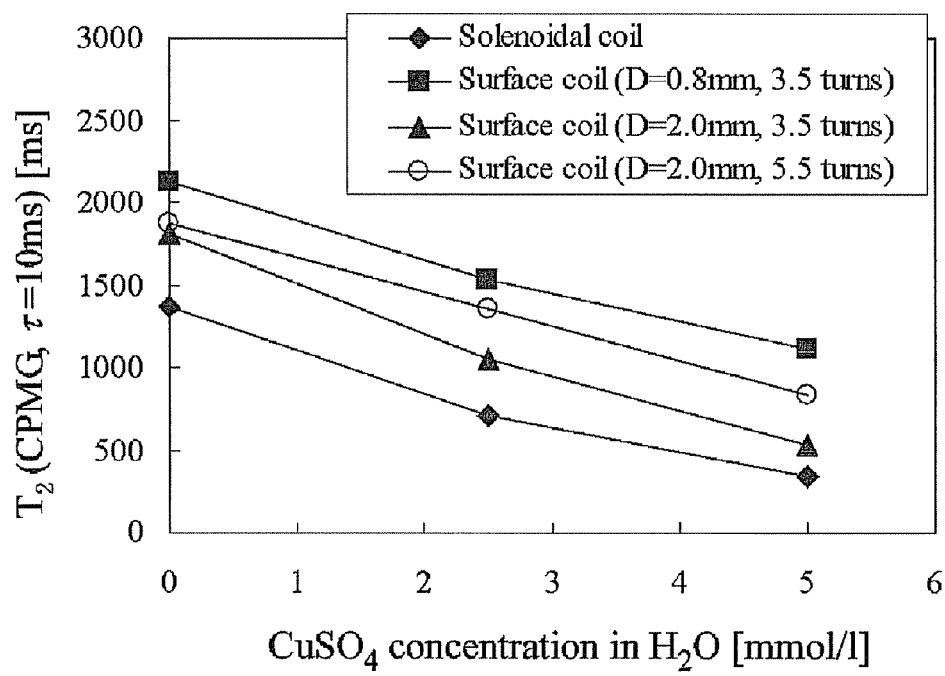
FIG. 18 is a drawing showing results of measurement of a multi-echo signal measured by the CPMG method in Example 1.

FIG. 18 is a drawing showing results of the measurement. The drawing shows also results of the measurement using the standard coil, for comparison with the small-sized coil.

As samples having different $T_2$ relaxation time constants, distilled water and a 1.2 mmol/l aqueous copper sulfate solution were used. Each sample was sealed into a container (inner size 15 mm×15 mm×gap 0.5 mm, thickness 0.12 mm) having the same geometry with the polymer membrane. The small-sized surface coil was attached to the center of the sample container, keeping a distance between the coil and the aqueous solution of 0.15 mm, including a polyimide film of 30 µm thick. The standard coil herein means a solenoid coil of 25 mm in diameter and 38 mm in length, sufficiently larger than the sample, and known to have an excellent irradiation uniformity of high frequency magnetic field, which is a standard type one having conventionally been used.

For the purpose of examining influences of diameter of the coil on the accuracy of measurement, two small-sized surface coils respectively having diameters of 0.8 mm and 2.0 mm were used for the measurement of $T_2$(CPMG) of the aqueous copper sulfate solutions. Results are shown in FIG. 19 and FIG. 20.

Figures 19, 20:
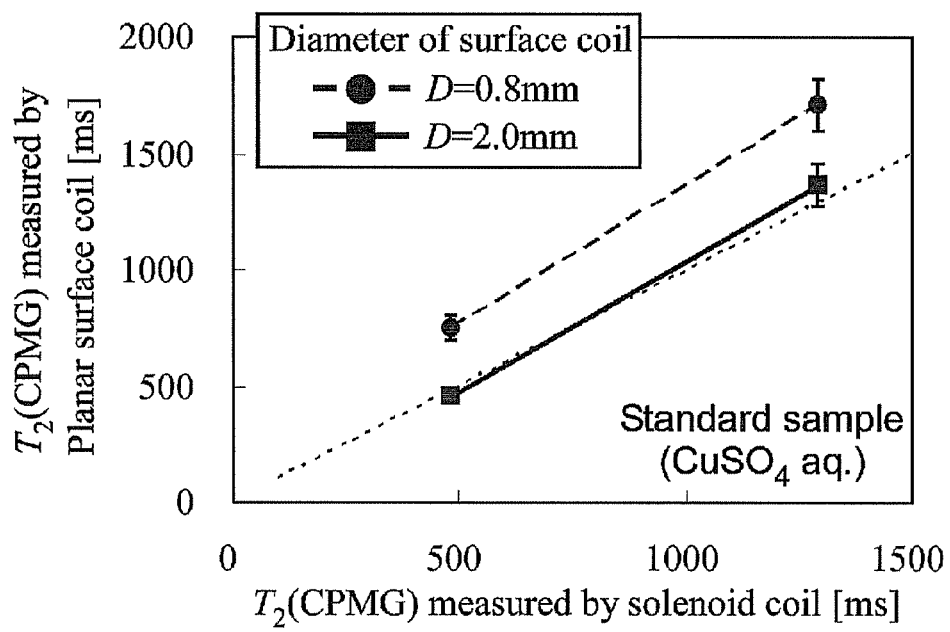
FIG. 19 is a drawing showing results of measurement of a multi-echo signal measured by the CPMG method in Example 2.
FIG. 20 is a drawing showing average values of calculated $T_2$ (CPMG), standard deviations expressing variations in measurement, and coefficients of variation obtained by dividing the standard deviations by the average values.

FIG. 20 shows, from the top to the bottom in this order, average values of $T_2$ (CPMG) obtained by the measurement repeated 10 to 20 times, ratios on the basis of average values $T_2$ (CPMG) obtained by the standard coil (numerals in parentheses), standard deviations expressing variations in the measurement, and coefficients of variation obtained by dividing the standard deviations by the average values.

The abscissa axis of FIG. 19 shows $T_2$(CPMG) measured by the standard coil using the same samples and under the same conditions, wherein the fine broken line in the drawing indicates the case where the $T_2$ (CPMG) was achieved similarly to as that obtained by the standard coil. The error bars indicate standard deviations (standards deviations listed in FIG. 20) of $T_2$(CPMG) calculated based on the measurement repeated 10 to 20 times.

From these drawings, the 2.0-mm diameter coil was found to give the same $T_2$(CPMG) as the standard coil, showing coefficients of variation of 0.11 to 0.13.

In contrast to this, the 0.8-mm-diameter coil was found to elongate the average values of the $T_2$(CPMG) 1.32 to 1.54 times as long as the $T_2$(CPMG) obtained by the standard coil. The 0.8-mm-diameter showed coefficients of variation of 0.14 to 0.16, showing increase from the coefficients of variation obtained by the 2.0-mm-diameter coil.

As is known from FIG. 19 and FIG. 20, the $T_2$ (CPMG) measured using the small-sized coil sometimes becomes longer than $T_2$(CPMG) measured using the standard coil. In this case, it is necessary to preliminarily calibrate the increment using a reference sample. As suggested by FIG. 20, the calibration may be accomplished using a constant calibration value, irrespective of the copper sulfate concentration. More specifically, $T_2$ (CPMG) is calculated by the CPMG method, the increment of $T_2$(CPMG) is then extracted from a preliminarily given table, based on the coil geometry, number of turns and other geometrical characteristics, and the correction for calibration is conducted either by subtracting a predetermined value from thus-obtained $T_2$ (CPMG), or by dividing it according to a predetermined ratio.

Downsizing of the coil may also lowers the NMR signal, and increases variation in the $T_2$ (CPMG). As has been described in the above, the coefficients of variation of the 0.8-mm-diameter coil were 0.14 to 0.16, showing increase from the coefficients of variation obtained by the 2.0-mm-diameter coil.

Why the $T_2$(CPMG) obtained by the 0.8-mm-diameter coil was elongated is supposedly because the diameter of the copper wire was thick enough to an unnegligible level as compared with the diameter of the coil, so that the excitation pulse intensity distribution became non-uniform within the measurement range, and a waveform by free induction decay after the 180° excitation pulse interfered with the echo, thereby resulting in apparent elongation of the $T_2$(CPMG).

Example 4

In this Example, the $T_2$ relaxation time constants of the polymer membranes were measured by the CPMG method, using the small-sized surface coil and the standard coil.

The polymer membrane same as those used in the referential example was used.

The small-sized surface coils used herein were those having diameters of 0.8 mm and 2.0 mm. Each of the small-sized surface coils is configured by winding a 50-μm-diameter lead wire having a polyurethane sheath, by the number of turns of 3.5 in a spiral form, and by holding the wire between tacky polyimide films of 30 μm thick so as to keep the geometry.

The polymer membrane was then subjected to the standardization treatment similarly to as in the referential example, and then stored as being immersed in distilled water at room temperature.

The polymer membrane was pressed to dry tissue paper for ten seconds, repeated three times, to as to remove water on the surface of the polymer membrane.

The polymer membrane was then held between two cover glasses (size 18 mm×18 mm×thickness 0.12 mm), and the circumference was sealed with a polyimide film so as to avoid dryness. The small-sized surface coil was attached at the center of the polyimide film, keeping a distance between the coil and the aqueous solution of 0.15 mm, including a polyimide film of 30 μm thick.

Temperature of the polymer membrane during the measurement was 23° C.

Figures 21, 22:
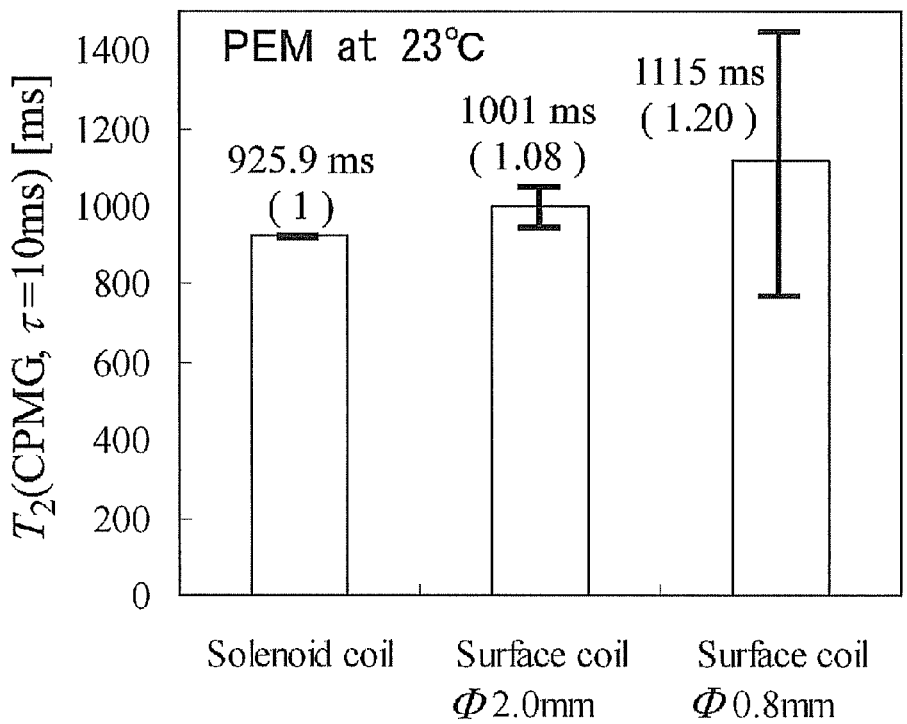
FIG. 21 is a drawing showing $T_2$ relaxation time constants calculated based on water-containing polymer membranes.
FIG. 22 is a drawing showing a table of results of $T_2$ relaxation time constants (CPMG) calculated in Example 4.

Results are shown in FIG. 21. Numerals shown in FIG. 21 are average values of the $T_2$ relaxation time constant (CPMG) obtained after repeating the measurement 10 times for each coil, and the numerals given in parentheses are ratios on the basis of the average value of the $T_2$ relaxation time constant (CPMG) obtained by using the standard coil. The error bars in the drawing indicate standard deviations of the measurement valued.

As is clear from FIG. 21, the 2.0-mm-diameter, small-sized surface coil was found to yield measurement values of the $T_2$ relaxation time constants (CPMG) almost equivalent to those obtained by the standard coil. The 0.8-mm-diameter, small-sized surface coil resulted in increase in the values of the $T_2$ relaxation time constants (CPMG), similarly to the measured results obtained using the aqueous copper sulfate solution in Example 2. The average value of the $T_2$ relaxation time constants measured using the 0.8-mm-diameter, small-sized surface coil was 1.20 times as large as the average value of the $T_2$ relaxation time constants (CPMG) obtained by using the standard coil.

As for variation in the measurement, the 2.0-mm-diameter, small-sized surface coil showed a standard deviation of 47 ms, and a coefficient of variation of 0.047, and the 0.8-mm-diameter, small-sized surface coil showed a standard deviation of 340 ms, and a coefficient of variation of 0.31.

Why the 0.8-mm-diameter, small-sized surface coil showed a larger variation in the measurement as compared with Example 2 is supposedly ascribable to a small intensity of the echo signal from the polymer membrane, and consequently to a large drop in the signal/noise ratio.

It is also found that ratio of the $T_2$ relaxation time constant (CPMG) obtained using the 0.8-mm-diameter, small-sized surface coil relative to the $T_2$ relaxation time constant (CPMG) obtained using the standard coil decreased as compared with Example 2.

As has been described also in Example 3, the ratio of the $T_2$ relaxation time constant (CPMG) obtained by using the small-sized surface coil relative to the $T_2$ relaxation time constant (CPMG) obtained by using the standard coil mainly depends on the diameter of the small-sized surface coil, and non-uniformity in the excitation intensity distribution as being affected by the geometry, so that it is considered that the small-sized surface coils of the same geometry should make the ratio constant.

Therefore, assuming this ratio as a correction factor relevant to the diameter of the small-sized surface coil, or the geometry of the small-sized surface coil, values of the $T_2$ relaxation time constant (CPMG) obtained by using the small-sized surface coil can be converted into the measurement values obtained by using the standard coil, by dividing the $T_2$ relaxation time constant (CPMG) obtained by using the small-sized surface coil by the ratio.

Example 4

In this Example, a plurality of small-sized surface coils were used in the instrument (FIG. 8) described in the second embodiment, so as to measure the samples based on a multiple-channel measurement system, and confirmed that the $T_2$(CPMG) values equivalent to those obtained by a large solenoid coil can be measured.

The small-sized RF coil 114 shown in FIG. 8 was fabricated by winding a 50-μm-diameter copper lead by the number of turns of 3.5, while keeping an outer diameter of 2.0 mm. In this Example, two coils are used, and respectively placed on the same sample. In the following description, a channel connected to one of two small-sized RF coils 114 will be referred to as a first channel, and the other as a second channel.

As the sample, an aqueous copper sulfate solution having a low concentration was used. A throughhole (15 mm×15 mm) was pierced at the center of an acrylic plate (18 mm×18 mm) of 0.5 mm thick, and cover glasses (18 mm×18 mm) of 0.12 mm thick were bonded on both sides thereof, to thereby fabricate a sample container having a gap of 0.5 mm. The aqueous copper sulfate solution was sealed in the container.

Two coils were placed on the cover glass of the sample container, as being approximately 5 mm away from each other, and the coil was further pressed to fix using an acrylic plate. Each coil was respectively connected with an LC resonant circuit oscillating at a resonance frequency (43.5 MHz).

The sample, two sets of coil and the resonant circuits are fixed in a coil holder, and inserted into the center portion of a magnet. The coil holder is lined with a copper foil of 0.05 mm thick on the inner surface thereof, so as to prevent the resonant circuit, containing two sets of coil and placed at the center thereof, from being interfered by the external noise.

The coil holder is disposed in the magnet (1-Tesla permanent magnet having a 45-mm air gap), and the signal lines of the individual channels are connected to a "send/receive change-over switch" (switching unit 161) and an "amplifier". Two sets of these components were used corresponding to the number of channels.

In this Example, a single "A/D converter board" was used for transmitting detected NMR signals to a PC. Therefore, a configuration adopted herein was such as making an output by adding the NMR signals from all channels, and receiving it by a single A/D converter board. If there are a plurality of A/D boards, and if a software capable of controlling them is available, the A/D boards can independently acquire their own NMR signals, and can calculate the $T_2$(CPMG) values for every channel.

For the case where only a single "A/D converter board" is used, any trial of receiving the NMR signals simultaneously from two channels may result in cross-talk of these signals. In this Example, the signals were therefore isolated from channel to channel, by shifting timing of the measurement of the individual channels. More specifically, the CPMG measurement was carried out on the first channel over a period from 0 second to 1 second, and the succeeding CPMG measurement was carried out on the second channel over a succeeding period from 1 second to 2 seconds.

From confirmation of the NMR signals presented by the measurement software, it was found that both of the first channel and the second channel causes attenuation of the NMR signals according to almost equivalent attenuation constants.

In this Example, an identical aqueous copper sulfate solution sealed in a single container was measured through two channels using two small-sized RF coils. Therefore, the $T_2$(CPMG) values measured on the individual channels should have the identical value.

FIG. 22 is a drawing showing a table containing results of calculation of the attenuation constants of the acquired NMR signals. As is clear from FIG. 22, measurement of $T_2$(CPMG) of the same sample using two sets of small-sized surface coil yielded almost same values. It can therefore be concluded that use of this system allows measurement of the $T_2$ (CPMG) distribution of the sample with the aid of a plurality of coils, demonstrating feasibility of array formation.

Example 5

In this example, the measurement instrument described in the first embodiment was used, and methanol content in the polymer membrane was measured.

[Samples]

In this embodiment, two polymer membranes shown below, differing in the methanol content, were measured.
polymer membrane having a methanol content of 30 mg
polymer membrane having a methanol content of 115 mg The polymer membranes used herein were polymer membranes (from Asahi Glass Co., Ltd, trade name "Flemion"), having a thickness of 500 μm in dry state, and a size of 11 mm×11 mm in dry state.

Paragraphs below will describe methods of preparing the samples.

[Method of Preparing of Polymer Membrane with Methanol Content of 115 mg]

First, a polymer membrane thoroughly dried using a drier was obtained. The polymer membrane in the dry state was then weighed (found to be 90 mg, in this case).

Next, the polymer membrane was immersed in methanol, and allowed to stand for one month or longer.

The polymer membrane immersed in methanol was weighed, and the obtained weight was subtracted by the dry mass of the polymer membrane, to thereby give the amount of methanol contained in the polymer membrane. The amount of methanol herein was found to be 115 mg.

The polymer membrane having a methanol content of 115 mg was found swelled, showing a thickness of 0.6 mm and a size of ca. 16 mm×ca.16 mm in plan view.

[Method of Preparing of Polymer Membrane with Methanol Content of 30 mg]

A polymer membrane thoroughly dried using a drier was obtained. The polymer membrane in the dry state was then weighed (found to be 90 mg, in this case).

Next, the polymer membrane immersed in methanol was moderately dried using a drier so as to adjust the methanol content of the polymer membrane.

The polymer membrane was then weighed, and the obtained weight was subtracted by the dry mass of the polymer membrane, to thereby give the amount of methanol contained in the polymer membrane. The amount of methanol herein was found to be 30 mg.

The polymer membrane having a methanol content of 30 mg was found to have a thickness of 0.5 mm and a size of ca. 11 mm×ca.11 mm in plan view.

[Configuration of Instrument]

The measurement instrument shown in the first embodiment was used.

The small-sized surface coil of the measurement instrument used herein was 2.0 mm in diameter, and 3.5 in the number of turns.

[Method of Measurement]

Using the CPMG method, intensity of every even-numbered echo signal was acquired, and the $T_2$ relaxation time constant (CPMG) was calculated, based on attenuation in the intensity.

In this measurement, the polymer membrane was held between two sheets of cover glass (0.12 mm thick), and the circumference was sealed with a polyimide film. This configuration can successfully prevent methanol from vaporizing from the polymer membrane.

Methanol content of the polymer membrane as measured by bringing the small-sized coil into contact with the cover glass.

Figure 23:
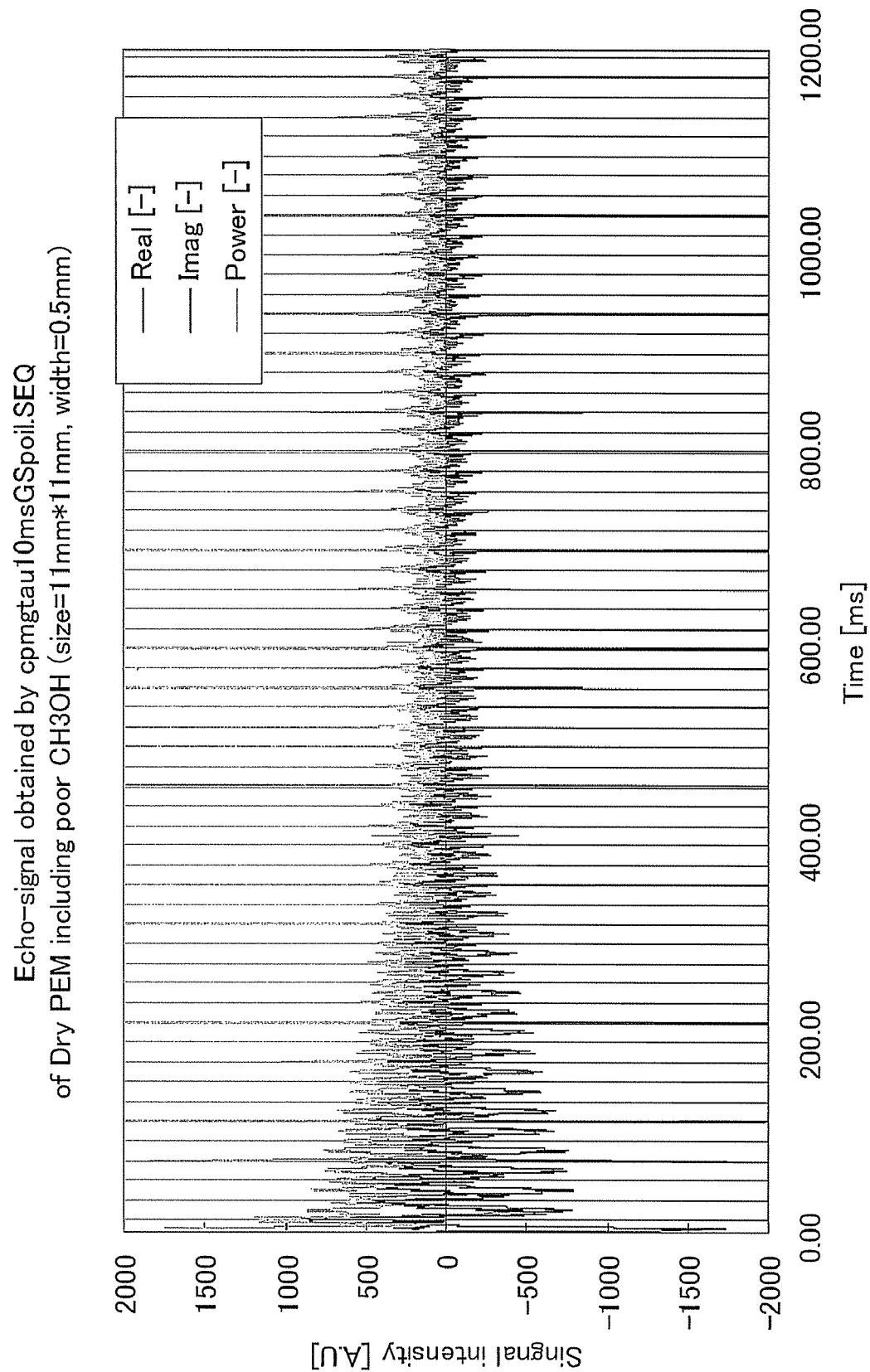
FIG. 23 is a drawing showing an attenuation curve of the echo signal in Example 5.

An example of the echo signal obtained from the polymer membrane having a methanol content of 30 mg is shown in FIG. 23.

$T_2$ relaxation time constant (CPMG) was then calculated based on the attenuation curve of the echo signal shown FIG. 23.

In this process, acquisition of the echo signal as shown in FIG. 23 was repeated 5 times, and calculation of the $T_2$ relaxation time constant (CPMG) was repeated 5 times. An average value of the $T_2$ relaxation time constant (CPMG) was found to be 428.5 ms, and the standard deviation was found to be 88.3 ms.

Next, $T_2$ relaxation time constant (CPMG) of the polymer membrane having a methanol content of 115 mg was measured.

Figure 24:
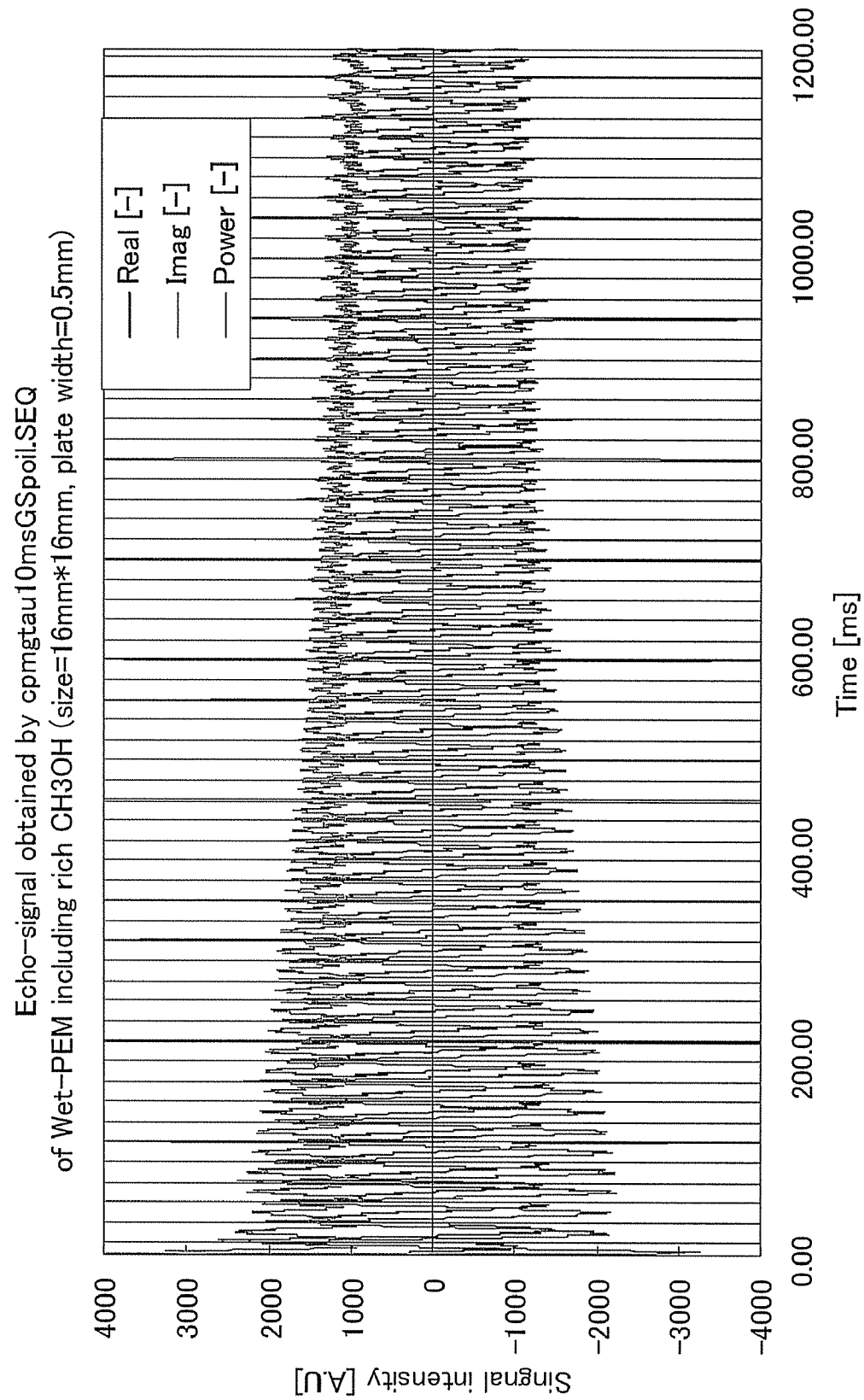
FIG. 24 is a drawing showing an attenuation curve of the echo signal in Example 5.

FIG. 24 shows an example of the echo signal obtained from the polymer membrane having a methanol content of 115 mg.

$T_2$ relaxation time constant (CPMG) was then calculated based on the attenuation curve of the echo signal shown in FIG. 24.

In this example, acquisition of the $T_2$ relaxation time constant (CPMG) from the polymer membrane having a methanol content of 115 mg was repeated 6 times. An average value of the $T_2$ relaxation time constant (CPMG) was found to be 1715.9 ms, and the standard deviation was found to be 359.1 ms.

Figure 25:
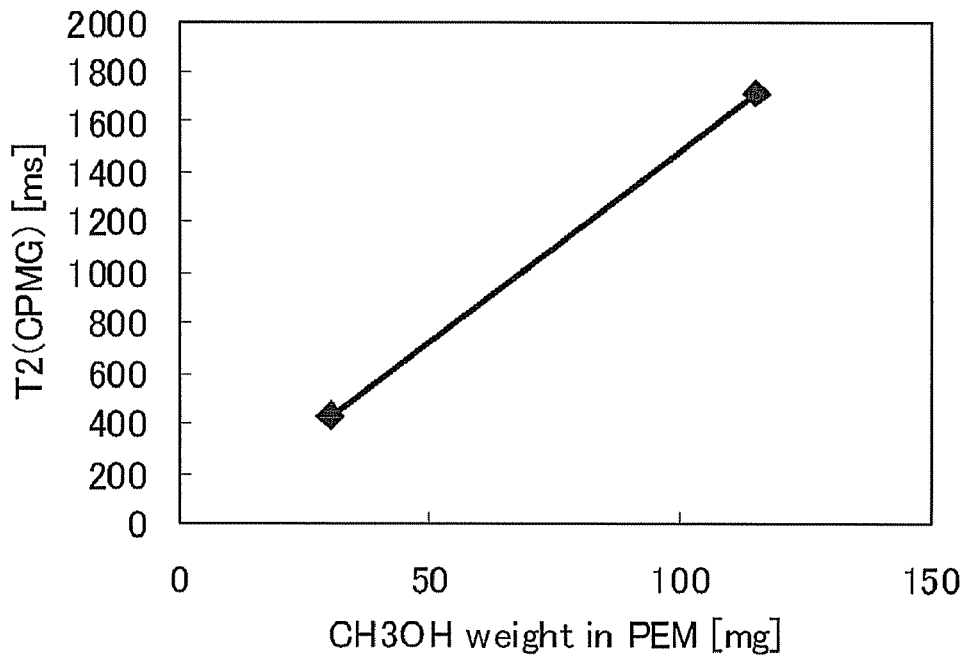
FIG. 25 is a drawing showing a relation between the amount of methanol contained in the polymer membrane and $T_2$ relaxation time constant.

FIG. 25 shows a relation between the methanol content of the polymer membrane and the $T_2$ relaxation time constant.

Figure 26:
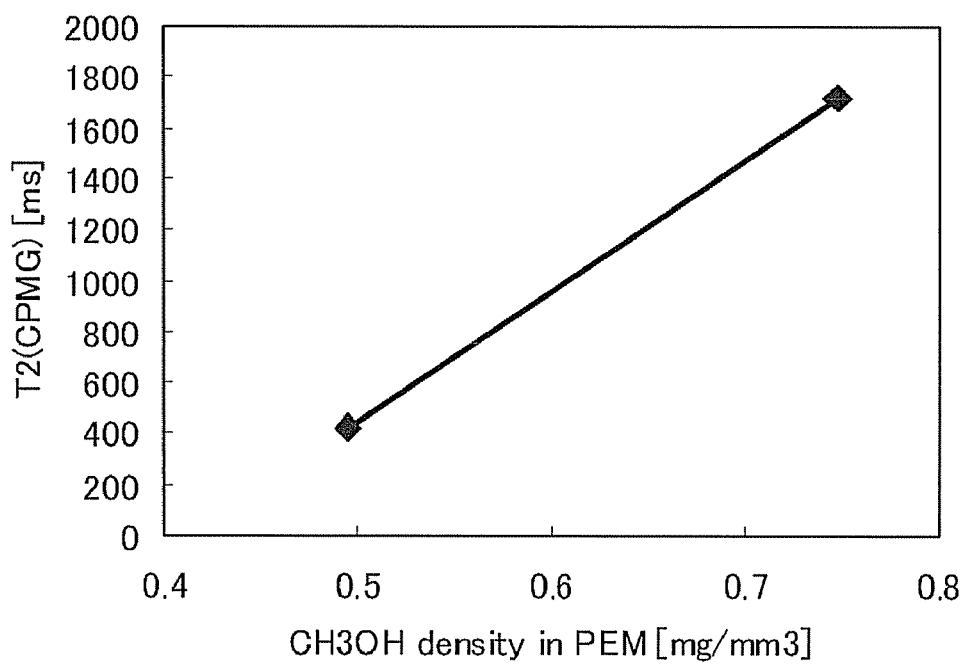
FIG. 26 is a drawing showing a relation between the amount ($mg/mm^3$) of methanol per unit volume and $T_2$ relaxation time constant.

Taking swelling of the polymer membrane due to absorption of methanol into consideration, FIG. 26 shows a relation between the methanol content per unit volume (mg/mm$^3$) and the $T_2$ relaxation time constant.

The $T_2$ relaxation time constant (CPMG) elongates as the methanol content increases, showing clear difference in the $T_2$ relaxation time constant (CPMG) between the high-methanol-concentration region and low-methanol-concentration region.

It is therefore made clear that the methanol content can be calculated by measuring the $T_2$ relaxation time constant by the CPMG method.

Advantages obtainable by the instrument and the method of this Example will be enumerated below.

First, the water content in the local region of the membrane, as large as the diameter of the coil, can be measured, using the small-sized RF coil attached to the polymer membrane.

Second, the measurement time of water content can be shortened within one second. In this Example, the $T_2$ relaxation time constant is measured by the CPMG method, using the spiral small-sized RF coil, so that the water content in the local region as large as the diameter of the coil can be measured with a high sensitivity within a time as short as one second or less. Although the 0.8-mm-diameter and 2.0-mm-diameter, small-sized RF coils were shown in this Example, any trial of further reducing the diameter may enable measurement of the water content in the polymer membrane in a fine-area.

Third, this Example makes use of changes in the $T_2$ relaxation time constant (CPMG) dependent to the water content owned by the polymer membrane, and can therefore realize measurement with an unprecedented sensitivity.

Fourth, by virtue of possibility of measuring the water content with a high accuracy within a short time, it is made possible to monitor the water content of the membrane, and to control the amount of supply of water vapor or water for swelling the membrane so as to adjust it to an appropriate water content.

Fifth, the small-sized RF coil, downsized to a level smaller than the thickness of the polymer membrane, enables measurement of the water content in the membrane only in the surficial portion thereof.

Sixth, by attaching the RF coil, smaller than the thickness of the polymer membrane, to both of the fuel side and oxidizer side of the polymer membrane, it is made possible to monitor the water content on both sides of the membrane, to know from which side the polymer membrane can more effectively be moistened by water vapor, and to allow more proper control of the water content of the membrane.

The foregoing paragraphs have described preferable embodiments and Examples referring to the drawings, merely as examples of the present invention, and allows any other various configurations other than those described in the above.

The foregoing embodiments and Examples have explained the exemplary cases in which the excitation-use oscillating magnetic field was applied in a form of high frequency pulse sequence, wherein excitation-use oscillating magnetic field is not limited thereto. For example, it is also allowable to adopt any other modes of embodiment, so far as they can acquire NMR signal group such as echo signal group and the like.

The sample stage 116 in the instrumental configuration shown in FIG. 5 may be deleted. For the case where the sample 115 is a constituent of certain product, water content of the constituent can locally be calculated, by disposing the small-sized RF coil 114 in the product.

The protic solvent content in the polymer membrane was measured in the foregoing embodiments and Examples, whereas besides this, it is also allowable to measure, for example, the amount of solvent (protic solvent) remaining in a photoresist film.

The photoresist film, formed over the surface to be coated, is generally heated to 100° C. to 200° C., and appropriately dried. By appropriately drying the photoresist film as described in the above, the photoresist film is successfully added with mechanical strength which is necessary in light exposure process.

When the photoresist film is softly baked, it is preferable to avoid complete drying of the solvent in the resist, but to allow a certain amount of the solvent to remain in the photoresist film, so that chemical reactions can appropriately proceed under light exposure. By understanding the amount of solvent remaining in the photoresist film by using the measurement instrument of the present invention, it is made possible to obtain a photoresist film having a desired solvent content.

Further, in the individual embodiments described in the above, the calibration curve table 126 was such as having, as stored therein by types of the samples, calibration curves expressing correlations between the water content of the samples and the $T_2$ relaxation time constant, but the table is not limited thereto.

For example, the calibration curve table 126 may have, as stored therein, information (calibration curves) expressing correlations between the protic solvent content contained in the samples by types of the protic solvents, and the $T_2$ relaxation time constant.

When the measurement instrument is used, the user enters information (types of protic solvent) specifying the protic solvent to be measured. The data acceptance unit 120 of the measurement instrument accepts the information, and sends it to the water content calculation unit 124.

When the protic solvent content is calculated by the water content calculation unit 124, a calibration curve corresponding to the type of the accepted protic solvent is acquired from the calibration curve table 126, and the protic solvent content in the sample is calculated.

The invention claimed is:

1. A method of locally measuring protic solvent content of a sample at a specific position thereof using a nuclear magnetic resonance method, comprising:
    a first step sequentially applying plural number of times an excitation-use oscillating magnetic field to a specific position of said sample disposed in a static magnetic field, using a small-sized RF coil smaller than said sample, and thereby obtaining a plurality of echo signals corresponded to said excitation-use oscillating magnetic field;
    a second step calculating a $T_2$ relaxation time constant based on intensity of said plurality of echo signals; and
    a third step of acquiring data expressing a correlation between the protic solvent content in said sample and the $T_2$ relaxation time constant, and determining said protic solvent content at the specific position in said sample, based on said data and said $T_2$ relaxation time constant calculated in the second step.

2. The method of measurement as claimed in claim 1, wherein said protic solvent is water.

3. The method of measurement as claimed in claim 2, using a planar coil as said small-sized RF coil.

4. The method of measurement as claimed in claim 2, wherein in said first step, said excitation-use oscillating magnetic field is applied according to a predetermined pulse sequence.

5. The method of measurement as claimed in claim 4, wherein in said first step, said excitation-use oscillating magnetic field is applied according to a pulse sequence composed of:
    (a) a 90° pulse; and
    (b) "n" 180° pulses which start after the elapse of time i following the pulse (a), applied at time 2τ intervals.

6. The method of measurement as claimed in claim 5, wherein said 90° pulse resides in a first phase; and
    said "n" 180° pulses reside in a second phase shifted 90° from said first phase.

7. The method of measurement as claimed in claim 5, wherein said pulse sequence in said first step and said third step contains a 180° pulse applied time τ earlier than said 90° pulse.

8. The method of measurement as claimed in claim 2, wherein in said first step, the excitation-use oscillating magnetic field is applied to a plurality of positions of said sample, using a plurality of said small-sized RF coils, so as to acquire echo signals corresponded to said excitation-use oscillating magnetic field;
    in said second step, the $T_2$ relaxation time constant is calculated for each of said plurality of positions of said sample; and
    in said third step, water content is determined for each of said plurality of positions of said sample, based on said $T_2$ relaxation time constant.

9. The method of measurement as claimed in claim 8, further comprising, posterior to said third step, a fourth step of presenting a water content distribution of said sample based on the water contents determined for said plurality of positions of said sample.

10. The method of measurement as claimed in claim 2, wherein said sample is a water-containing membrane.

11. An instrument of locally measuring protic solvent content of a sample at a specific position thereof using a nuclear magnetic resonance method, comprising:
    a static magnetic field application unit applying a static magnetic field to said sample;
    a small-sized RF coil smaller than said sample, applying an excitation-use oscillating magnetic field to said sample, and acquiring an echo signal corresponded to said excitation-use oscillating magnetic field;
    and an operation unit calculating a $T_2$ relaxation time constant based on intensity of said echo signal, and calculating said protic solvent content of said sample at the specific position thereof, based on said calculated $T_2$ relaxation time constant.

12. The measurement instrument as claimed in claim 11, wherein said protic solvent is water.

13. The measurement instrument as claimed in claim 12, wherein said small-sized RF coil is a planar coil.

14. The measurement instrument as claimed in claim 11, wherein said small-sized RF coil is a planar coil which comprises a coil portion having a right-handed lead wire, and a coil portion having a left-handed lead wire, linked to each other.

15. The measurement instrument as claimed in claim 11, further comprising a support supporting said small-sized RF coil and said static magnetic field application unit,
    wherein said support has a stick form, and has said small-sized RF coil attached to the end portion thereof.

16. The measurement instrument as claimed in claim 12, further comprising a storage unit keeping, by types of the samples, information expressing a correlation between the water content of said sample and the $T_2$ relaxation time constant,
    wherein said operation unit acquires said information corresponded to the sample to be measured from said storage unit, and calculates the water content based on the information.

17. The measurement instrument as claimed in claim 12, wherein said small-sized RF coil applies said excitation-use oscillating magnetic field according to a predetermined pulse sequence.

18. The measurement instrument as claimed in claim 17, wherein said small-sized RF coil applies said excitation-use oscillating magnetic field according to a pulse sequence composed of:
    (a) a 90° pulse; and
    (b) "n" 180° pulses which start after the elapse of time τ following the pulse (a), applied at time 2τ intervals.

19. The measurement instrument as claimed in claim 18, wherein said 90° pulse resides in a first phase; and
said "n" 180° pulses reside in a second phase shifted from said first phase.

20. The measurement instrument as claimed in claim 18, wherein said pulse sequence contains a 180° pulse applied time τ earlier than said 90° pulse.

21. The measurement instrument as claimed in claim 12, configured as further having a plurality of said small-sized RF coils, allowing said plurality of small-sized RF coils to apply an excitation-use oscillating magnetic field to a plurality of positions of said sample, and acquiring an echo signal corresponded to said excitation-use oscillating magnetic field; and
allowing said operation unit to calculate the water content at each of the plurality of positions of said sample.

22. The measurement instrument as claimed in claim 21, further comprising an output unit presenting a water content distribution of said sample,
wherein said operation unit calculates the water content distribution of said sample based on the water contents determined for said plurality of positions of said sample,
and said output unit presents said water content distribution calculated by said operation unit.

23. The measurement instrument as claimed in claim 12, wherein said operation unit comprises:
a calculation unit calculating a calculated value of water content based on intensity of said echo signal; and
a correction unit calculating said water content, by correcting said calculated value of water content, corresponding to the size of said small-sized RF coil.

24. The measurement instrument as claimed in claim 12, further comprising:
an RF signal generation unit generating an RF signal which allows said small-sized RF coil to generate said excitation-use oscillating magnetic field;
an echo signal detection unit detecting the echo signal acquired by said small-sized RF coil, and sending said echo signal to said operation unit; and
a switching circuit provided at a branching portion to which said small-sized RF coil, said RF signal generation unit and said echo signal detection unit are connected, and toggled between a state of connection of said small-sized RF coil and said RF signal generation unit, and a state of connection of said small-sized RF coil and said echo signal detection unit.

25. The measurement instrument as claimed in claim 11, having a plurality of said small-sized RF coils, and further comprising an output unit presenting a protic solvent content distribution of said sample,
said plurality of small-sized RF coils apply the excitation-use oscillating magnetic field to the plurality of positions of said sample, so as to acquire echo signals corresponded to said excitation-use oscillating magnetic field;
said operation unit calculates the protic solvent content at each of said plurality of positions of said sample; and
said output unit has a measurement data acquisition unit acquiring the protic solvent content for each of said plurality of positions of said sample, calculated by said operation unit; and
a display unit displaying the protic solvent contents acquired by said measurement data acquisition unit, in partitioned regions on a single screen.

26. The method of measurement as claimed in claim 1, wherein said sample is a polymer membrane.

27. The method of measurement as claimed in claim 1, wherein said protic solvent is methanol.

28. The measurement instrument as claimed in claim 11, wherein said sample is a polymer membrane.

29. The measurement instrument as claimed in claim 11, wherein said protic solvent is methanol.

30. A fuel cell system comprising:
a fuel cell composed of a polymer membrane, and anode and cathode opposed while placing the polymer membrane in between;
an oxidizing gas supply unit supplying an oxidizing gas to the fuel cell;
a fuel gas supply unit supplying a fuel gas to the fuel cell;
a water vapor mixing unit mixing water vapor with the fuel gas discharged from the fuel gas supply unit towards the fuel cell, and supplying the fuel gas and the water vapor to the fuel cell;
the measurement instruments as claimed in any one of claims 11 to 25, 28, and 29 measuring water content of the polymer membrane; and
a control unit acquiring results of measurement of water content sent from the measurement instrument, and controlling the water vapor mixing unit based on the results of measurement, so as to adjust the amount of supply of water vapor to be supplied from the water vapor mixing unit.

* * * * *